(12) United States Patent
Chan Chun Kong et al.

(10) Patent No.: US 7,351,713 B2
(45) Date of Patent: Apr. 1, 2008

(54) SPIROHYDANTOIN COMPOUNDS AND METHODS FOR THE MODULATION OF CHEMOKINE RECEPTOR ACTIVITY

(75) Inventors: Laval Chan Chun Kong, Kirkland (CA); Ming-Qiang Zhang, Cherry Hinton (GB); Christophe Moinet, Montreal (CA); Marc Courchesne, Laval (CA); Thumkunta Jagadeeswar Reddy, Pierrefonds (CA); Melanie Proulx, Strasbourg (FR)

(73) Assignee: Viro Chem Pharma, Inc., Laval (CA)

( * ) Notice: Subject to any disclaimer, the term of this patent is extended or adjusted under 35 U.S.C. 154(b) by 202 days.

(21) Appl. No.: 10/937,878

(22) Filed: Sep. 10, 2004

(65) Prior Publication Data

US 2005/0075360 A1    Apr. 7, 2005

Related U.S. Application Data

(60) Provisional application No. 60/501,420, filed on Sep. 10, 2003.

(51) Int. Cl.
*A61K 31/438* (2006.01)
*C07D 471/10* (2006.01)

(52) U.S. Cl. .................. 514/278; 546/20; 544/124; 514/231.5

(58) Field of Classification Search ............. 514/278, 514/231.5; 546/20; 544/124
See application file for complete search history.

(56) References Cited

U.S. PATENT DOCUMENTS

| | | | |
|---|---|---|---|
| 5,646,172 A | 7/1997 | Claussner et al. | |
| 5,705,654 A | 1/1998 | Claussner et al. | |
| 5,739,336 A * | 4/1998 | Weinhardt et al. | 546/20 |
| 5,958,936 A | 9/1999 | Claussner et al. | |
| 6,291,469 B1 | 9/2001 | Fisher et al. | |
| 6,528,534 B2 | 3/2003 | Fisher et al. | |
| 6,693,109 B2 | 2/2004 | Fisher et al. | |

FOREIGN PATENT DOCUMENTS

| | | |
|---|---|---|
| EP | 0 704 448 | 4/1996 |
| EP | 1013276 | 6/2000 |
| WO | WO 96/24582 | 8/1996 |
| WO | WO 97/11940 | 4/1997 |
| WO | WO 0038680 | 7/2000 |
| WO | WO 0039125 | 7/2000 |
| WO | WO 0187839 | 11/2001 |
| WO | WO 0190106 | 11/2001 |
| WO | WO 02070479 | 9/2002 |
| WO | WO 02076948 | 10/2002 |
| WO | WO 02079156 | 10/2002 |
| WO | WO 03/020721 | 3/2003 |
| WO | WO 03042177 | 5/2003 |
| WO | WO 03084954 | 11/2003 |
| WO | WO 2004/092169 | 10/2004 |
| WO | WO 2004092169 | 10/2004 |

OTHER PUBLICATIONS

Int'l Search Report and the Written Opinion of the Int'l. Searching Authority, issued Feb. 1, 2005 in PCT Application No. PCT/CA2004/001657.
Chemical Abstract 73:98869 (1970).
Chemical Abstract 131:214230 (1999).
C.L. Wysong et al . *J. Org. Chem*. 1996, 61, 7650-7651.
P.W. Smith et al. *J. Med. Chem*. 1995, 38, 3772-3779.
M.J. McKennon et al . *J.Org. Chem*. 1993, 58, 3568-3571.

* cited by examiner

*Primary Examiner*—Charanjit S. Aulakh
(74) *Attorney, Agent, or Firm*—Millen, White, Zelano, Branigan, P.C.

(57) ABSTRACT

Compounds of formula I

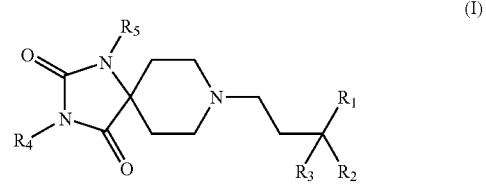

wherein $R_1$, $R_2$, $R_3$, $R_4$ and $R_5$ are as defined herein, or pharmaceutically acceptable salts, hydrates or solvates thereof, are useful for the modulation of CCR5 chemokine receptor activity.

39 Claims, No Drawings

SPIROHYDANTOIN COMPOUNDS AND METHODS FOR THE MODULATION OF CHEMOKINE RECEPTOR ACTIVITY

This application claims benefit of U.S. Provisional Application Ser. No. 60/501,420, filed Sep. 10, 2003, the entire disclosure of which is hereby incorporated by reference.

FIELD OF THE INVENTION

The present invention relates to novel spirohydantoin compounds and a method of modulating chemokine receptor activity using these compounds. The present invention is also directed to novel spirohydantoin compounds which are useful in the prevention or treatment of diseases associated with the modulation of CCR5 chemokine receptor activity. The present invention is further directed to a method of blocking cellular entry of HIV in a subject and to compositions using these compounds.

BACKGROUND OF THE INVENTION

Chemokines are chemotactic cytokines that are released by a wide variety of cells to attract macrophages, T cells, eosinophils, basophils and neutrophils to sites of inflammation and they also play a role in the maturation of cells of the immune system. Chemokines play an important role in immune and inflammatory responses in various diseases and disorders, including asthma, rhinitis and allergic diseases, as well as autoimmune pathologies such as rheumatoid arthritis and atherosclerosis. Chemokines are small 70 to 80 amino acid proteins with well-characterized three-dimensional structures, usually stabilized by two disulfide bridges. They are divided into four families on the basis of pattern of conserved cysteine residues. Chemokine receptors have been designated such as, CCR1, CCR2, CCR2A, CCR2B, CCR3, CCR4, CCR5, CCR6, CCR7, CCR8, CCR9, CCR10, CXCR1, CXCR2, CXCR3, and CXCR4 and therefore agents which modulate these receptors may be useful in the prevention and treatment of diseases as mentioned above.

One of them, the C—C chemokines family, includes potent chemoattractants of monocytes and lymphocytes such as RANTES (Regulated on Activation, Normal T Expressed and Secreted), eotaxin, MIP-1α and MIP-1β (Macrophage Inflammatory Proteins) and human monocyte chemotactic proteins 1-3 (MCP-1, MCP-2 and MCP-3). More specifically, C—C chemokine receptor 5 (CCR5), a β-chemokine receptor with a seven-transmembrane-protein structure, was found to serve as a coreceptor for non-syncytium-inducing or macrophage-tropic HIV-1 (R5 viruses). It was also established that CCR5 is the principal chemokine receptor required for the entry of HIV into the cell during primary infection. Therefore, interfering with the interaction between the viral receptor CCR5 and HIV can block HIV entry into the cell. It would therefore be useful to provide novel compounds which are modulators of chemokine receptor activity.

SUMMARY OF THE INVENTION

In one aspect, the present invention provides novel compounds represented by formula (I):

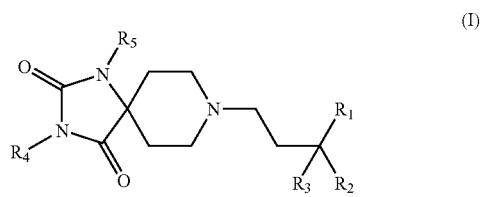

or pharmaceutically acceptable salts, hydrates or solvates thereof, wherein $R_1$ is H, OH, optionally substituted $C_{1-10}$ alkyl (e.g. $C_{1-6}$ alkyl), optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, $NR_8R_9$, optionally substituted O—$C_{1-6}$ alkyl, optionally substituted O—$C_{6-12}$ aryl, optionally substituted O—$C_{6-12}$ aralkyl (e.g. O—$C_{7-12}$ aralkyl),

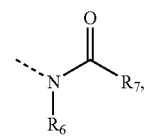

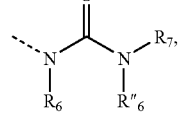

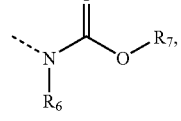

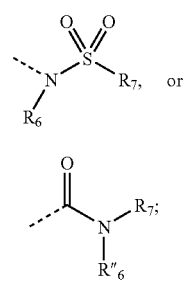

$R_2$ is optionally substituted $C_{1-10}$ alkyl (e.g. $C_{1-6}$ alkyl), optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl or optionally substituted 3 to 10 membered heterocycle;

$R_3$ is H, optionally substituted $C_{1-10}$ alkyl (e.g. $C_{1-6}$ alkyl), optionally substituted $C_{2-10}$ alkenyl (e.g. $C_{2-6}$ alkenyl), optionally substituted $C_{2-10}$ alkynyl (e.g. $C_{2-6}$ alkynyl), or optionally substituted $C_{6-12}$ aryl;

$R_4$ and $R_5$ are each independently H, optionally substituted $C_{1-10}$ alkyl, optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, optionally substituted $C_{6-12}$ aralkyl (e.g. $C_{7-12}$ aralkyl) or optionally substituted 3 to 10 membered heteroaralkyl (e.g. heteroaralkyl having a 3 to 9 membered heterocyclic group and a $C_{1-6}$ alkylene group);

$R_6$ and $R''_6$ are each independently H, optionally substituted $C_{1-10}$ alkyl (e.g. $C_{1-4}$ alkyl), optionally substituted $C_{2-10}$ alkenyl (e.g. $C_{2-4}$ alkenyl), or optionally substituted $C_{2-10}$ alkynyl (e.g. $C_{2-4}$ alkynyl); and $R_7$ is H, optionally substituted $C_{1-10}$ alkyl (e.g. $C_{1-6}$ alkyl), optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, optionally substituted $C_{6-12}$ aralkyl (e.g. $C_{7-12}$ aralkyl) or optionally substituted 3 to 10 membered heteroaralkyl (e.g. heteroaralkyl having a 3 to 9 membered heterocyclic group and a $C_{1-6}$ alkylene group), or $R''_6$ and $R_7$ can be taken together to form an optionally substituted 3 to 10 membered heterocycle; and $R_8$ and $R_9$ are each independently H, optionally substituted $C_{1-10}$ alkyl (e.g. $C_{1-6}$ alkyl), optionally substituted $C_{2-10}$ alkenyl (e.g. $C_{2-6}$ alkenyl), or optionally substituted $C_{2-10}$ alkynyl (e.g. $C_{2-6}$ alkynyl).

According to a further aspect, the present invention provides novel compounds represented by formula (I) wherein $R_1$ is chosen from

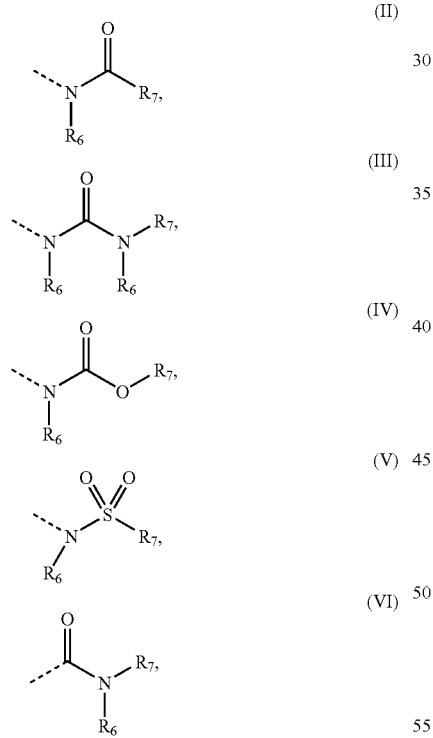

H, $C_{1-6}$ alkyl, $C_{6-12}$ aryl, OH, $NR_8R_9$, O—$C_{1-6}$ alkyl, O—$C_{6-12}$ aryl or O—$C_{6-12}$ aralkyl;

$R_2$ is chosen from $C_{1-10}$ alkyl, $C_{6-12}$ aryl or 3 to 10 membered heterocycle;

$R_3$ is chosen from H, $C_{1-6}$ alkyl or $C_{6-12}$ aryl;

$R_4$ is chosen from H, $C_{1-6}$ alkyl, $C_{6-12}$ aryl, 3 to 10 membered heterocycle, $C_{6-12}$ aralkyl or $C_{3-10}$ heteroaralkyl;

$R_5$ is chosen from H or $C_{1-6}$ alkyl;

$R_6$ is chosen from H or $C_{1-4}$ alkyl and $R_7$ is chosen from H, $C_{1-10}$ alkyl, $C_{6-12}$ aryl, 3 to 10 membered heterocycle, $C_{6-12}$ aralkyl or 3 to 10 membered heteroaralkyl or $R_6$ and $R_7$ can be taken together to form a 3 to 10 membered heterocycle;

$R_8$ and $R_9$ are each independently chosen from H or $C_{1-6}$ alkyl.

In another aspect, there is provided a method of modulating chemokine receptor activity in a subject comprising administering to the subject a therapeutically effective amount of a compound of formula (I) or composition of the invention.

In still another aspect, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In still another aspect, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject comprising administering to the subject in need thereof a therapeutically effective amount of a compound of formula (I) or composition of the invention to block HIV from cellular entry in said subject.

In still another aspect, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In another aspect, there is provided a pharmaceutical formulation comprising the compound of the invention in combination with a pharmaceutically acceptable carrier or excipient.

In another aspect of the invention is the use of a compound according to formula (I), for the manufacture of a medicament for the prevention or treatment of diseases associated with the modulation of chemokine receptor activity.

DETAILED DESCRIPTION OF THE INVENTION

In one embodiment, compounds of the present invention comprise those wherein the following embodiments are present, either independently or in combination.

In one embodiment, the present invention provides novel compounds represented by formula (I):

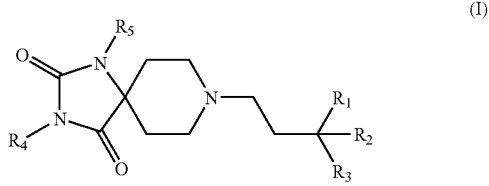

or pharmaceutically acceptable salts, hydrates or solvates thereof wherein $R_1$, $R_2$, $R_3$, $R_4$ and $R_5$ are defined above.

In one embodiment, the compounds of the present invention are in the (S)-enantiomer as represented by formula (Ia):

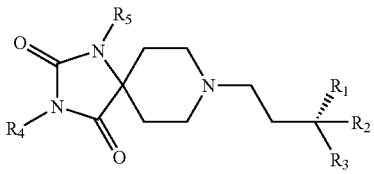
(Ia)

or pharmaceutically acceptable salts, hydrates or solvates thereof wherein $R_1$, $R_2$, $R_3$, $R_4$ and $R_5$ are defined above.

In a further embodiment, $R_1$ is chosen from:

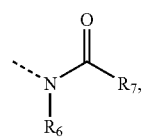
(II)

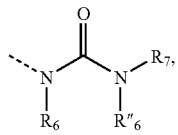
(III)

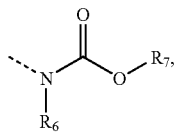
(IV)

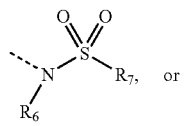
(V)

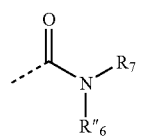
(VI)

In a further embodiment, $R_1$ is:

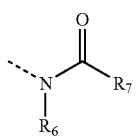
(II)

wherein $R_6$ is as defined above and $R_7$ is chosen from optionally substituted $C_{1-10}$ alkyl, $C_{6-12}$ aryl or optionally substituted 3 to 10 membered heterocycle.

In a further embodiment, $R_1$ is:

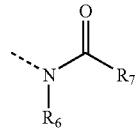
(II)

wherein:
$R_7$ is methyl;
$R_7$ is ethyl;
$R_7$ is isopropyl;
$R_7$ is cyclopropyl;
$R_7$ is cyclobutyl;
$R_7$ is cyclopentyl;
$R_7$ is cyclohexyl;
$R_7$ is cycloheptyl;
$R_7$ is 4,4-difluorocyclohexyl;
$R_7$ is $CH_2$-cyclopropyl;
$R_7$ is $CH_2$-cyclobutyl;
$R_7$ is $CH_2$-cyclopentyl;
$R_7$ is $CH_2$-cyclohexyl.
$R_7$ is phenyl;
$R_7$ is phenyl substituted with at least one methyl;
$R_7$ is phenyl substituted with at least one halogen;
$R_7$ is phenyl substituted with at least one Cl;
$R_7$ is phenyl substituted with at least one Br;
$R_7$ is phenyl substituted with at least one F;
$R_7$ is phenyl substituted with at least one methoxy.
$R_7$ is benzyl;
$R_7$ is benzyl substituted with at least one methyl;
$R_7$ is benzyl substituted with at least one halogen;
$R_7$ is benzyl substituted with at least one Cl;
$R_7$ is benzyl substituted with at least one Br;
$R_7$ is benzyl substituted with at least one F;
$R_7$ is benzyl substituted with at least one methoxy.
$R_7$ is pyridine.

In a further embodiment, $R_1$ is:

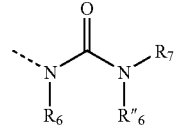
(III)

wherein $R_6$ and $R''_6$ are as defined above and $R_7$ is optionally substituted $C_{6-12}$ aryl, or $R''_6$ and $R_7$ can be taken together to form an optionally substituted 3 to 10 membered heterocycle.

In a further embodiment, $R_1$ is:

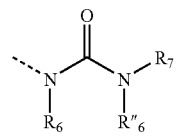
(III)

wherein:
$R_7$ is phenyl;
$R_7$ is phenyl substituted with at least one methyl;

$R_7$ is phenyl substituted with at least one halogen;
$R_7$ is phenyl substituted with at least one Cl;
$R_7$ is phenyl substituted with at least one Br;
$R_7$ is phenyl substituted with at least one F;
$R_7$ is phenyl substituted with at least one methoxy.
$R_7$ is naphthyl.
$R''_6$ and $R_7$ can be taken together to form an optionally substituted piperidine.
$R''_6$ and $R_7$ can be taken together to form an optionally substituted morpholine.
$R''_6$ and $R_7$ can be taken together to form a morpholine.
$R''_6$ and $R_7$ can be taken together to form an optionally substituted pyrrolidine.
$R''_6$ and $R_7$ can be taken together to form a 3,3-difluoropyrrolidine.

In a further embodiment, $R_1$ is:

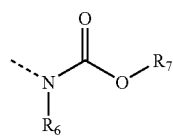

(IV)

wherein $R_6$ is as defined above and $R_7$ is optionally substituted $C_{1-10}$ alkyl.

In a further embodiment, $R_1$ is:

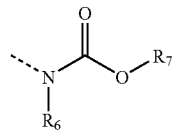

(IV)

wherein:
$R_7$ is methyl;
$R_7$ is ethyl;
$R_7$ is tert-butyl;
$R_7$ is cyclobutyl;
$R_7$ is cyclopentyl;
$R_7$ is cyclohexyl.

In a further embodiment, $R_1$ is:

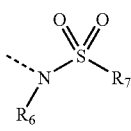

(V)

wherein $R_6$ is as defined above and $R_7$ is chosen from optionally substituted $C_{1-10}$ alkyl, optionally substituted $C_{6-12}$ aryl or optionally substituted 3 to 10 membered heterocycle.

In a further embodiment, $R_1$ is:

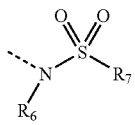

(V)

wherein:
$R_7$ is optionally substituted phenyl;
$R_7$ is optionally substituted $C_{1-10}$ alkyl;

In a further embodiment, $R_1$ is:

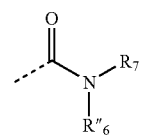

(VI)

wherein $R''_6$ is as defined above and $R_7$ is chosen from optionally substituted $C_{1-10}$ alkyl or optionally substituted $C_{6-12}$ aryl.

In a further embodiment, $R_1$ is:

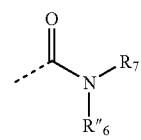

(VI)

wherein:
$R_7$ is cyclohexyl;
$R_7$ is phenyl.

In a further embodiment, $R_2$ is chosen from optionally substituted $C_{6-12}$ aryl or optionally substituted 3 to 10 membered heterocycle.

In further embodiments:
$R_2$ is optionally substituted $C_{6-12}$ aryl.
$R_2$ is phenyl;
$R_2$ is phenyl substituted with at least one halogen;
$R_2$ is phenyl substituted with at least one Cl;
$R_2$ is phenyl substituted with at least one F;
$R_2$ is phenyl substituted with at least one methoxy.

In a further embodiment:
$R_2$ is optionally substituted 3 to 10 membered heterocycle.
$R_2$ is thienyl.
$R_2$ is pyridyl.

In a further embodiment, $R_3$ is chosen from H or optionally substituted $C_{1-4}$ alkyl.

In one embodiment, $R_3$ is H.
In one embodiment, $R_3$ is methyl.
In one embodiment, $R_4$ is chosen from $C_{6-12}$ aralkyl (e.g. $C_{7-12}$ aralkyl) or a 3 to 10 membered heteroaralkyl (e.g. heteroaralkyl having a 3 to 9 membered heterocyclic group and a $C_{1-6}$ alkylene group).

In a further embodiment, $R_4$ is optionally substituted $C_{6-12}$ aralkyl (e.g. $C_{7-12}$ aralkyl).

In a further embodiment, $R_4$ is optionally substituted 3 to 10 membered heteroaralkyl (e.g. heteroaralkyl having a 3 to 9 membered heterocyclic group and a $C_{1-6}$ alkylene group).

In further embodiments:
$R_4$ is benzyl;
$R_4$ is benzyl substituted with at least one halogen;
$R_4$ is benzyl substituted with at least one Br;
$R_4$ is benzyl substituted with at least one F;
$R_4$ is benzyl substituted with at least one Cl;
$R_4$ is benzyl substituted with a $C_{1-3}$ alkoxy;
$R_4$ is benzyl substituted with methoxy;
$R_4$ is benzyl substituted with $SO_2C_{1-3}$alkyl;
$R_4$ is benzyl substituted with methanesulfonyl;
$R_4$ is benzyl substituted with difluoromethoxy;
$R_4$ is benzyl substituted with trifluoromethoxy;
$R_4$ is benzyl substituted with trifluoromethyl;
$R_4$ is benzyl substituted with CN;
$R_4$ is benzyl substituted with pyrrazoyl;
$R_4$ is benzyl optionally substituted in the para (p) position;
$R_4$ is pyridinyl-methyl.

In one embodiment, $R_5$ is chosen from H, optionally substituted $C_{1-4}$ alkyl, optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, optionally substituted $C_{6-12}$ aralkyl (e.g. $C_{7-12}$ aralkyl) or optionally substituted 3 to 10 membered heteroaralkyl (e.g. heteroaralkyl having a 3 to 9 membered heterocyclic group and a $C_{1-6}$ alkylene group).

In a further embodiment, $R_5$ is chosen from H or optionally substituted $C_{1-4}$ alkyl.

In one embodiment, $R_5$ is H.
In further embodiments:
$R_5$ is methyl;
$R_5$ is ethyl;
$R_5$ is isopropyl.

In a further embodiment, $R_5$ is optionally substituted $C_{2-10}$ alkenyl (e.g. $C_{2-6}$ alkenyl) or optionally substituted $C_{2-10}$ alkynyl (e.g. $C_{2-6}$ alkynyl).

In one embodiment, $R_5$ is allyl.

In a further embodiment, $R_5$ is optionally substituted $C_{6-12}$ aryl or optionally substituted 3 to 10 membered heterocycle. In one embodiment, $R_5$ is phenyl.

In a further embodiment, $R_5$ is optionally substituted $C_{6-12}$ aralkyl (e.g. $C_{7-12}$ aralkyl) or optionally substituted 3 to 10 membered heteroaralkyl (e.g. heteroaralkyl having a 3 to 9 membered heterocyclic group and a $C_{1-6}$ alkylene group). In one embodiment, $R_5$ is benzyl.

The compounds of the present invention may have an asymmetric center. As two optical isomers can independently be obtained from each asymmetric center, compounds of the invention having one asymmetric center can be in the form of the enantiomers, i.e., the (+) enantiomer or (−) enantiomer, in pure or partially purified form, as well as mixtures of enantiomers.

In one embodiment, the compounds of the present invention are the (+) enantiomer having an enantiomeric excess of 99%.

In one embodiment, the compounds of the present invention are the (+) enantiomer having an enantiomeric excess of 95%.

In one embodiment, the compounds of the present invention are the (+) enantiomer having an enantiomeric excess of 90%.

In one embodiment, the compounds of the present invention are the (−) enantiomer having an enantiomeric excess of 99%.

In one embodiment, the compounds of the present invention are the (−) enantiomer having an enantiomeric excess of 95%.

In one embodiment, the compounds of the present invention are the (−) enantiomer having an enantiomeric excess of 90%.

Compounds of the present invention have also two asymmetric centers. As two optical isomers can independently be obtained from each asymmetric center, compounds of the invention having two asymmetric centers can be in the form of the diastereomers. It is intended that all the possible diastereomers in mixtures and as pure or partially purified compounds are included in this invention.

In one embodiment, the compounds of the present invention are in the form of the (R,R)-diastereomer;
In one embodiment, the compounds of the present invention are in the form of the (S,R)-diastereomer;
In one embodiment, the compounds of the present invention are in the form of the (R,S)-diastereomer;
In one embodiment, the compounds of the present invention are in the form of the (S,S)-diastereomer.

In one embodiment, the compounds of the present invention are a (R,R)-diastereomer having an optical purity in excess of 99%.

In one embodiment, the compounds of the present invention are a (R,R)-diastereomer having an optical purity in excess of 95%.

In one embodiment, the compounds of the present invention are a (R,R)-diastereomer having an optical purity in excess of 90%.

In one embodiment, the compounds of the present invention are a (S,R)-diastereomer having an optical purity in excess of 99%.

In one embodiment, the compounds of the present invention are a (S,R)-diastereomer having an optical purity in excess of 95%.

In one embodiment, the compounds of the present invention are a (S,R)-diastereomer having an optical purity in excess of 90%.

In one embodiment, the compounds of the present invention are a (R,S)-diastereomer having an optical purity in excess of 99%.

In one embodiment, the compounds of the present invention are a (R,S)-diastereomer having an optical purity in excess of 95%.

In one embodiment, the compounds of the present invention are a (R,S)-diastereomer having an optical purity in excess of 90%.

In one embodiment, the compounds of the present invention are a (S,S)-diastereomer having an optical purity in excess of 99%.

In one embodiment, the compounds of the present invention are a (S,S)-diastereomer having an optical purity in excess of 95%.

In one embodiment, the compounds of the present invention are a (S,S)-diastereomer having an optical purity in excess of 90%.

In one embodiment, there is provided a method of modulating chemokine receptor activity in a subject comprising administering to the subject a therapeutically effective amount of a compound of formula (I) or composition of the invention.

In another embodiment, there is provided a method for the prevention or treatment of diseases associated with the modulation of chemokine receptor activity in a subject in need of such treatment comprising administering to the subject a therapeutically effective amount of a compound of formula (I) or composition of the invention.

In a further embodiment, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In another embodiment, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject in need thereof comprising administering to the subject a therapeutically effective amount of a compound of formula (I) to block HIV from cellular entry in said subject.

In still another aspect, there is provided a method for prevention or treatment of HIV infections in a subject in need of such treatment comprising administering to the subject a therapeutically effective amount of a compound of formula (I) or composition of the invention.

In still another aspect, there is provided a method for delaying the onset of AIDS or treating AIDS in a subject in need of such treatment comprising administering to the subject a therapeutically effective amount of a compound of formula (I) or composition of the invention.

In a further embodiment, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In a further embodiment, there is provided a method for the prevention or treatment of diseases associated with the modulation of CCR5 chemokine receptor activity in a subject in need of such treatment comprising administering to the subject a pharmaceutical combination comprising at least one compound of formula (I) and at least one further therapeutic agent.

In still another aspect, there is provided a method for blocking cellular entry of HIV in a subject or for the prevention or treatment of HIV infections in a subject in need of such treatment comprising administering to the subject a pharmaceutical combination comprising at least one compound of formula (I) and at least one further therapeutic agent.

In still another aspect, there is provided a method for delaying the onset of AIDS or treating AIDS in a subject in need of such treatment comprising administering to the subject a pharmaceutical combination comprising at least one compound of formula (I) and at least one further therapeutic agent.

In another embodiment, there is provided a combination useful for the prevention or treatment of diseases associated with the modulation of chemokine receptor activity which is a therapeutically effective amount of a compound of formula (I) and therapeutically effective amount of at least one further therapeutic agent.

In one embodiment, combinations of the present invention comprise those wherein the following embodiments are resent, either independently or in combination.

In a further embodiment, the pharmaceutical combinations of this invention may contain at least one further therapeutic agent chosen from an agent used in inflammatory diseases, immunoregulatory diseases and in organ transplantation reactions.

In another embodiment, the pharmaceutical combination of this invention may contain at least one further therapeutic agent which is an antiviral agent.

In one embodiment, the pharmaceutical combination of this invention may contain at least one further antiviral agent which is chosen from nucleoside and nucleotide analog reverse transcriptase inhibitors, non-nucleoside reverse transcriptase inhibitors, protease inhibitors, attachment and fusion inhibitors, integrase inhibitors or maturation inhibitors.

In one embodiment, the pharmaceutical combinations of this invention may contain at least one other antiviral agent which is a nucleoside and nucleotide analog reverse transcriptase inhibitors chosen from 3TC (lamivudine, Epivir®), AZT (zidovudine, Retrovir®), Emtricitabine (Coviracil®, formerly FTC), d4T (2',3'-dideoxy-2',3'-didehydro-thymidine, stavudine and Zerit®), tenofovir (Viread®), 2',3'-dideoxyinosine (ddI, didanosine, Videx®), 2',3'-dideoxycytidine (ddC, zalcitabine, Hivid®), Combivir® (AZT/3TC or zidovudine/lamivudine combination), Trivizir® (AZT/3TC/abacavir or zidovudine/lamivudine/abacavir combination), abacavir (1592U89, Ziagen®), SPD-754, ACH-126,443 (Beta-L-Fd4C), Alovudine (MIV-310), DAPD (amdoxovir), Racivir, 9-[(2-hydroxymethyl)-1,3-dioxolan-4-yl]guanine or 2-amino-9-[(2-hydroxymethyl)-1,3-dioxolan-4-yl]adenine.

In another embodiment, the pharmaceutical combination of this invention may contain at least one other antiviral agent which is a non-nucleoside reverse transcriptase inhibitor chosen from Nevirapine (Viramune®, NVP, BI-RG-587), delavirdine (Rescriptor®, DLV), efavirenz (DMP 266, Sustiva®), (+)-Calanolide A, Capravirine (AG1549, formerly S-1153), DPC083, MIV-150, TMC120, TMC125 or BHAP (delavirdine), calanolides or L-697,661 (2-Pyridinone 3benzoxazolMeNH derivative).

In another embodiment, the pharmaceutical combination of this invention may contain at least one other antiviral agent which ia a protease inhibitor chosen from nelfinavir (Viracept®, NFV), amprenavir (141W94, Agenerase®), indinavir (MK-639, IDV, Crixivan®), saquinavir (Invirase®, Fortovase®, SQV), ritonavir (Norvir®, RTV), lopinavir (ABT-378, Kaletra®), Atazanavir (BMS232632), mozenavir (DMP-450), fosamprenavir (GW433908), RO033-4649, Tipranavir (PNU-140690), TMC114 or VX-385.

In another embodiment, the pharmaceutical combination of this invention may contain at least one other antiviral agent which is an attachment and fusion inhibitor chosen from T-20 (enfuvirtide, Fuzeon®), T-1249, Schering C(SCH-C), Schering D (SCH-D), FP21399, PRO-140, PRO 542, PRO 452, TNX-355, GW873140 (AK602), TAK-220, UK-427,857 or soluble CD4, CD4 fragments, CD4-hybrid molecules, BMS-806, BMS-488043, AMD3100, AMD070 or KRH-2731.

In another embodiment, the pharmaceutical combination of this invention may contain at least one other antiviral agent which is an integrase inhibitor chosen from S-1360, L-870,810, L-870,812 or C-2507.

In another embodiment, the pharmaceutical combination of this invention may contain at least one other antiviral agent which is a maturation inhibitor and is PA-457.

In another embodiment, the pharmaceutical combination of this invention may contain at least one other antiviral agent which is a zinc finger inhibitor and is azodicarbonamide (ADA).

In another embodiment, the pharmaceutical combination of this invention may contain at least one other antiviral agent which is an antisense drug and is HGTV43.

In another embodiment, the pharmaceutical combination of this invention may contain at least one other antiviral agent which is an immunomodulator, immune stimulator or cytokine chosen from interleukin-2 (IL-2, Aldesleukin, Proleukin), granulocyte macrophage colony stimulating factor (GM-CSF), erythropoietin, Multikine, Ampligen, thymomodulin, thymopentin, foscarnet, HE2000, Reticulose, Murabutide, Resveratrol, HRG214, HIV-1 Immunogen (Remune) or EP HIV-1090.

In another embodiment, the pharmaceutical combination of this invention may contain at least one other antiviral agent chosen from 2',3'-dideoxyadenosine, 3'-deoxythymidine, 2',3'-dideoxy-2',3'-didehydrocytidine and ribavirin; acyclic nucleosides such as acyclovir, ganciclovir; interferons such as alpha-, beta- and gamma-interferon; glucuronation inhibitors such as probenecid; or TIBO drugs, HEPT, TSAO derivatives.

The combinations referred to above may conveniently be presented for use in the form of a pharmaceutical formulation and thus pharmaceutical formulations comprising a combination as defined above together with a pharmaceutically acceptable carrier thereof comprises a further aspect of the invention.

The individual components of such combinations may be administered either sequentially or simultaneously in separate or combined pharmaceutical formulations.

In a further embodiment, the said compound of formula (I) and said therapeutic agent are administered sequentially.

In a further embodiment, the said compound of formula (I) and said therapeutic agent are administered simultaneously.

The subject to which the compounds are administered can be, for example, a mammal or a human. Preferably, the subject is a human.

In one embodiment, the present invention further provides a pharmaceutical composition comprising at least one compound having the formula (I) or pharmaceutically acceptable salts or pharmaceutically acceptable hydrates or pharmaceutically acceptable solvates thereof and at least one pharmaceutically acceptable carrier or excipient.

In another embodiment, the invention provides the use of a compound having the formula (I) for the manufacture of a medicament for prevention and treatment of diseases associated with the modulation of CCR5 chemokine receptor activity in a host comprising administering a therapeutically effective amount of a compound of formula (I).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety having, for example, 1 to 10 carbon atoms, and is optionally substituted. For example, suitable substituents include halogen, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $C(O)NR_{29}R_{30}$ (wherein $R_{29}$ is H or $C_{1-6}$ alkyl and $R_{30}$ is selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{31}R_{32}$, $NR_{31}SO_2R_{32}$ (wherein $R_{31}$, and $R_{32}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{33})NR_{34}$ or $C(R_{33})NOR_{34}$ (wherein $R_{33}$ and $R_{34}$ are each independently selected from the group consisting of H, $C_{1-6}$ alkyl, or $C_{6-12}$ aryl).

Preferred substituents for the alkyl groups include halogen (Br, Cl, I or F), cyano, nitro, oxo, amino, COOH, COO—$C_{1-4}$ alkyl, CO—$C_{1-4}$ alkyl, and phenyl.

Examples of alkyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, cyclopropyl, cyclobutyl, cycloheptyl, and cyclohexyl, which in each case are unsubstituted or optionally substituted one or more times by, for example, halogen (Br, Cl, I or F), cyano, nitro, oxo, amino, COOH, COO—$C_{1-4}$ alkyl, CO—$C_{1-4}$ alkyl, and/or phenyl.

The term alkyl also includes alkyls in which one or more hydrogen atom is replaced by a halogen, i.e. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The term "alkenyl" refers to alkyl groups may have one or more double bonds in the chain. The term "alkynyl" refers to alkyl groups may have one or more triple bonds in their chain. The alkenyl and alkynyl groups can be optionally substituted as described above for the alkyl groups.

Preferred substituents for the alkenyl and alkynyl groups include halogen (Br, Cl, I or F), cyano, nitro, oxo, amino, COOH, COO—$C_{1-4}$ alkyl, CO—$C_{1-4}$ alkyl, and phenyl.

Examples of alkenyl and alkynyl groups include but are not limited to allyl, vinyl, acetylenyl, ethylenyl, propenyl, isopropenyl butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclohexenyl, and cyclohexdienyl, which in each case are unsubstituted or optionally substituted one or more times by, for example, halogen (Br, Cl, I or F), cyano, nitro, oxo, amino, COOH, COO—$C_{1-4}$ alkyl, CO—$C_{1-4}$ alkyl, and/or phenyl.

The term "alkoxy" or "O—$C_{x-y}$ alkyl" (e.g., O—$C_{1-6}$ alkyl) represents an alkyl which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy. The alkoxy groups can be optionally substituted as described above for the alkyl groups.

Preferred substituents for the alkoxy groups include halogen (Br, Cl, I or F), cyano, nitro, oxo, amino, COOH, COO—$C_{1-4}$ alkyl, CO—$C_{1-4}$ alkyl, and phenyl.

The term "alkylamino" represents an alkyl which is covalently bonded to the adjacent atom through a nitrogen atom and may be monoalkylamino or dialkylamino, wherein the alkyl groups may be the same or different. Examples include but are not limited to methylamino, dimethylamino, ethylamino, diethylamino, methylethylamino, propylamino, isopropylamino, butylamino, isobutylamino, sec-butylamino, tert-butylamino, pentylamino, isopentylamino, neopentylamino, tert-pentylamino, hexylamino, isohexylamino and neohexylamino.

The term "alkyloxycarbonyl" represents an alkyloxy which is covalently bonded to the adjacent atom through carbonyl (C=O). Examples include but are not limited to methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl and neohexyloxycarbonyl.

The term "amidino" represents —$C(=NR_{10})NR_{11}R_{12}$, wherein $R_{10}$, $R_{11}$ and $R_{12}$ are each independently selected from H, $C_{1-6}$ alkyl, $C_{6-12}$ aryl or $C_{6-12}$ aralkyl (e.g. $C_{7-12}$ aralkyl), or $R_{11}$ and $R_{12}$ are taken together with the nitrogen to which they are attached to form a 3 to 10 membered heterocycle.

The term "amido" represents —$CONH_2$, —$CONHR_{13}$ and —$CONR_{13}R_{14}$ wherein $R_{13}$ and $R_{14}$ are each independently selected from $C_{1-6}$ alkyl, $C_{6-12}$ aryl, 3 to 10 membered heterocycle or $C_{6-12}$ aralkyl (e.g. $C_{7-12}$ aralkyl), or $R_{13}$ and $R_{14}$ are taken together with the nitrogen to which they are attached to form a 3 to 10 membered heterocycle.

The term "amino" represents a derivative of ammonia obtained by substituting one or more hydrogen atom and include —$NH_2$, —$NHR_{15}$ and —$NR_{15}R_{16}$, wherein $R_{15}$ and $R_{16}$ are each independently selected from $C_{1-6}$ alkyl, $C_{6-12}$ aryl or $C_{6-12}$ aralkyl (e.g. $C_{7-12}$ aralkyl), or $R_{15}$ and $R_{16}$ are taken together with the nitrogen to which they are attached to form a 3 to 10 membered heterocycle.

The term "aryl" represents a carbocyclic moiety containing at least one benzenoid-type ring (i.e. the aryl group may be monocyclic or polycyclic), and which is optionally substituted with one or more substituents. For example, suitable substituents include halogen, halogenated $C_{1-6}$ alkyl, halogenated $C_{1-6}$ alkoxy, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{6-12}$aralkyl (e.g. $C_{7-12}$ aralkyl), $C_{1-6}$alkoxy, $C_{6-12}$aralkyloxy (e.g. $C_{7-12}$ aralkyloxy), $C_{6-12}$aryloxy, 3 to 10 membered heterocycle, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $C(O)NR_{29}R_{30}$ (wherein $R_{29}$ is H or $C_{1-6}$ alkyl and $R_{30}$ is selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{31}R_{32}$, $NR_{31}SO_2R_{32}$ (wherein $R_{31}$ and $R_{32}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{33})NR_{34}$ or $C(R_{33})NOR_{34}$ (wherein $R_{33}$ and $R_{34}$ are each independently selected from the group consisting of H, $C_{1-6}$ alkyl, or $C_{6-12}$ aryl).

Preferred substituents for the aryl groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of aryl include but are not limited to phenyl, tolyl, dimethylphenyl, aminophenyl, anilinyl, naphthyl, anthryl, phenanthryl or biphenyl, which in each case is unsubstituted or substituted one or more times by, for example, halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "aryloxy" represents an aryl which is covalently bonded to the adjacent atom through an oxygen atom. The aryloxy groups can be optionally substituted as described above for the aryl groups.

Preferred substituents for the aryloxy groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of aryloxy include but are not limited to phenoxy and naphthyloxy, which in each case is unsubstituted or substituted one or more times by, for example, halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-14}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "aralkyl" represents an aryl group attached to the adjacent atom by a $C_{1-6}$ alkyl. The arylalkyl groups can be optionally substituted as described above for the aryl groups.

Preferred substituents for the arylalkyl groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of arylalkyl include but are not limited to benzyl, benzhydryl, trityl, phenethyl, 3-phenylpropyl, 2-phenylpropyl, 4-phenylbutyl and naphthylmethyl, which in each case is unsubstituted or substituted one or more times by, for example, halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "aralkyloxy" represents an aralkyl which is covalently bonded to the adjacent atom through an oxygen atom. The arylalkyloxy groups can be optionally substituted as described above for the aryl groups.

Preferred substituents for the arylalkyloxy groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples or arylalkyloxy include but are not limited to benzyloxy, benzhydryloxy, trityloxy, phenethyloxy, 3-phenylpropyloxy, 2-phenylpropyloxy, 4-phenylbutyloxy and naphthylmethoxy, which in each case is unsubstituted or substituted one or more times by, for example, halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "guanidino" represents —$NR_{17}C(=NR_{18})NR_{19}R_{20}$ wherein $R_{17}$, $R_{18}$, $R_{19}$ and $R_{20}$ are each independently selected from H, $C_{1-6}$ alkyl, $C_{6-12}$ aryl or $C_{6-12}$ aralkyl (e.g. $C_{7-12}$ aralkyl), or $R_{19}$ and $R_{20}$ are taken together with the nitrogen to which they are attached to form a 3 to 10 membered heterocycle.

The term "urea" represents —$N(R_{33})CONR_{34}R_{35}$ wherein $R_{33}$ is H or $C_{1-6}$ alkyl and wherein $R_{34}$ and $R_{35}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl), or $R_{34}$ and $R_{35}$ are taken together with the nitrogen to which they are attached to form a 3 to 10 membered heterocycle.

The term "halogen" is specifically a fluoride atom, chloride atom, bromide atom or iodide atom.

The term "heterocycle" represents an optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, suitable substituents include halogen, halogenated $C_{1-6}$ alkyl, halogenated $C_{1-6}$ alkoxy, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{6-12}$aralkyl (e.g. $C_{7-12}$ aralkyl), $C_{1-6}$alkoxy, $C_{6-12}$ aryl, $C_{6-12}$aralkyloxy, $C_{6-12}$aryloxy, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle), $NR_{29}C(O)R_{30}$, $C(O)NR_{29}R_{30}$ (wherein $R_{29}$ is H or $C_{1-6}$ alkyl and $R_{30}$ is selected from H, $C_{1-6}$ alkyl, $C_{6-12}$ aryl, $C_{6-12}$ aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle), $SO_2NR_{31}R_{32}$, $NR_{31}SO_2R_{32}$ (wherein $R_{31}$ and $R_{32}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)), $C(R_{33})NR_{34}$ or $C(R_{33})NOR_{34}$ (wherein $R_{33}$ and $R_{34}$ are each independently selected from the group consisting of H, $C_{1-6}$ alkyl, or $C_{6-12}$ aryl).

Preferred substituents for the heterocycle groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl, which in each case is unsubstituted or substituted one or more times by, for example, halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "heteroaralkyl" represents a heterocycle group attached to the adjacent atom by a $C_{1-6}$ alkyl. The heteroaralkyl groups can be optionally substituted as described above for the heteroaryl groups.

Preferred substituents for the heteroarylalkyl groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

The term "independently" means that a substituent can be the same or a different definition for each item.

The term "optionally substituted" means that respective group can optionally be substituted by one or more halogen, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{6-12}$aralkyl (e.g. $C_{7-12}$ aralkyl), $C_{6-12}$ aryl, $C_{1-6}$alkoxy, $C_{6-12}$aralkyloxy (e.g. $C_{7-12}$ aralkyloxy), $C_{6-12}$aryloxy, 3 to 10 membered heterocycle, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{6-12}$ aralkyl (e.g. $C_{7-12}$ aralkyl) or 3 to 10 membered heterocycle) $NR_{29}C(O)R_{30}$ (wherein $R_{29}$ is H or $C_{1-6}$alkyl and $R_{30}$ is selected from H, $C_{1-6}$alkyl, $C_{6-12}$ aryl, $C_{6-12}$aralkyl (e.g. $C_{7-12}$ aralkyl) or 3 to 10 membered heterocycle, or $R_{29}$ and $R_{30}$ are taken together with the atoms to which they are attached to form a 3 to 10 membered heterocycle) or $SO_2NR_{31}R_{32}$ (wherein $R_{31}$ and $R_{32}$ are each independently selected from the group consisting of H, $C_{1-6}$ alkyl, $C_{6-12}$ aryl, 3 to 10 membered heterocycle and $C_{6-12}$ aralkyl (e.g. $C_{7-12}$ aralkyl)).

"Oxidation levels": When there is a sulfur atom present, the sulfur atom can be at different oxidation levels, ie. S, SO, or $SO_2$. All such oxidation levels are within the scope of the present invention. When there is a nitrogen atom present, the nitrogen atom can be at different oxidation levels, ie. N or NO. All such oxidation levels are within the scope of the present invention.

There is also provided "enantiomers" and "diastereoisomers" of the present invention. It will be appreciated that the compounds in accordance with the present invention can contain one or more chiral centers. The compounds in accordance with the present invention may thus exist in the form of two different optical isomers, that is (+) or (−) enantiomers or in the form of different diastereoisomers. All such enantiomers, diastereoisomers and mixtures thereof, including racemic or other ratio mixtures of individual enantiomers and diastereoisomers, are included within the scope of the invention. The single diastereoisomers can be obtained by methods well known to those of ordinary skill in the art, such as HPLC, crystallization and chromatography. The single enantiomer can be obtained by methods well known to those of ordinary skill in the art, such as chiral HPLC, enzymatic resolution and chiral auxiliary derivatization.

The optical purity is numerically equivalent to the "enantiomeric excess". The term "enantiomeric excess" is defined in percentage (%) value as follows: [mole fraction (major enantiomer)–mole fraction (minor enantiomer)]×100. An example of enantiomeric excess of 99% represents a ratio of 99.5% of one enantiomer and 0.5% of the opposite enantiomer.

There is also provided "pharmaceutically acceptable hydrates" of the compounds of the present invention. "Hydrates" exist when the compound of the invention incorporates water. The hydrate may contain one or more molecule of water per molecule of compound of the invention. Illustrative non-limiting examples include monohydrate, dihydrate, trihydrate and tetrahydrate. The hydrate may contain one or more molecule of compound of the invention er molecule of water. An illustrative non-limiting example includes semi-hydrate. In one embodiment, the water may be held in the crystal in various ways and thus, the water molecules may occupy lattice positions in the crystal, or they may form bonds with salts of the compounds as described herein. The hydrate must be "acceptable" in the sense of not eing deleterious to the recipient thereof. The hydration may be assessed by methods known in the art such as Loss on Drying techniques (LOD) and Karl Fisher titration.

There is also provided "pharmaceutically acceptable salts" of the compounds of the present invention. By the term "pharmaceutically acceptable salts" of compounds are meant those derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal, alkaline earth metal or ammonium salts. The salt(s) must be "acceptable" in the sense of not being deleterious to the recipient thereof. Non-limiting examples of such salts known by those of ordinary skill in the art include without limitation calcium, potassium, sodium, choline, ethylenediamine, tromethamine, arginine, glycinelycine, lycine, magnesium and meglumine.

There is also provided a "pharmaceutically acceptable solvates" of the compounds of the present invention. The term "solvate" means that the compound of the invention incorporates one or more pharmaceutically acceptable solvent. The solvate may contain one or more molecule of solvent per molecule of compound of the invention or may contain one or more molecule of compound of the invention per molecule of solvent. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

Reference hereinafter to a compound according to the invention includes compounds of the general formula (I) and their pharmaceutically acceptable salts, hydrates and solvates.

"Polymorphs": It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC), differential thermal analysis (DTA), thermogravimetric analysis (TGA)), Raman spectroscopy, comparative intrinsic dissolution rate, scanning electron microscopy (SEM).

In one aspect, the present invention provides novel compounds including:

Compound 1 3-(4-Bromobenzyl)-8-(3-phenyl-propyl)-1,3,8-triaza-spiro[4.5]decane-2,4-dione hydrochloride Compound 2 3-(4-Bromobenzyl)-8-(3-phenyl-butyl)-1,3,8-triaza-spiro[4.5]decane-2,4-dione hydrochloride Compound 3 3-(4-Bromobenzyl)-8-(3,3-diphenyl-propyl)-1,3,8-triaza-spiro[4.5]decane-2,4-dione hydrochloride Compound 4 {3-[3-(4-Bromo-benzyl)-2,4-dioxo-1,3,8-triaza-spiro[4.5]dec-8-yl]-1-(S)-phenyl-propyl}-carbamic acid tert-butyl ester Compound 5 8-(3-(S)-Amino-3-phenyl-propyl)-3-(4-bromo-benzyl)-1,3,8-triaza-spiro[4.5]decane-2,4-dione Compound 6 (S)-3-(4-Bromobenzyl)-8-(3-isobutyrylamino-3-phenyl-propyl)-2,4-dioxo-1,3,8-triaza-spiro[4.5]decane hydrochloride Compound 7 (S)-3-(4-Bromobenzyl)-8-[3-(cyclopentanecarbonyl-amino)-3-phenyl-propyl]-2,4-dioxo-1,3,8-triaza-spiro[4.5]decane hydrochloride Compound 8 (S)-3-(4-Bromobenzyl)-8-[3-(cyclohexanecarbonyl-amino)-3-phenyl-propyl]-2,4-dioxo-1,3,8-triaza-spiro[4.5]decane hydrochloride Compound 9 Cyclopentanecarboxylic acid {3-(S)-[3-(4-methoxy-benzyl)-2,4-dioxo-1,3,8-triaza-spiro[4.5]dec-8-yl]-1-phenyl-propyl}-amide hydrochloride Compound 10 Cyclopropanecarboxylic acid {3-(S)-[3-(4-methoxy-benzyl)-2,4-dioxo-1,3,8-triaza-spiro[4.5]dec-8-yl]-1-phenyl-propyl}-amide hydrochloride Compound 11 N-{(S)-3-[3-(4-Bromo-benzyl)-2,4-dioxo-1,3,8-triaza-spiro[4.5]dec-8-yl]-1-phenyl-propyl}-benzamide hydrochloride Compound 12 N-{(S)-3-[3-(4-Bromo-benzyl)-2,4-dioxo-1,3,8-triaza-spiro[4.5]dec-8-yl]-1-phenyl-propyl}-2-phenyl-acetamide hydrochloride Compound 13 N-{(S)-3-[3-(4-Bromo-benzyl)-2,4-dioxo-1,3,8-triaza-spiro[4.5]dec-8-yl]-1-phenyl-propyl}-nicotinamide hydrochloride Compound 14 N-{(S)-3-[3-(4-Bromo-benzyl)-2,4-dioxo-1,3,8-triaza-spiro[4.5]dec-8-yl]-1-phenyl-propyl}-acetamide hydrochloride Compound 15 N-{(S)-3-[3-(4-Bromo-benzyl)-2,4-dioxo-1,3,8-triaza-spiro[4.5]dec-8-yl]-1-phenyl-propyl}-propionamide hydrochloride Compound 16 N-{(S)-3-[3-(4-Bromo-benzyl)-2,4-dioxo-1,3,8-triaza-spiro[4.5]dec-8-yl]-1-phenyl-propyl}-2,2-dimethyl-propionamide hydrochloride Compound 17 Cyclopropanecarboxylic acid {(S)-3-[3-(4-bromo-benzyl)-2,4-dioxo-1,3,8-triaza-spiro[4.5]dec-8-yl]-1-phenyl-propyl}-amide hydrochloride Compound 18 1-Methyl-cyclopropanecarboxylic acid {(S)-3-[3-(4-bromo-benzyl)-2,4-dioxo-1,3,8-triaza-spiro[4.5]dec-8-yl]-1-phenyl-propyl}-amide hydrochloride Compound 19 N-{(S)-3-[3-(4-Bromo-benzyl)-2,4-dioxo-1,3,8-triaza-spiro[4.5]dec-8-yl]-1-phenyl-propyl}-2-cyclopropyl-acetamide hydrochloride Compound 20 Cyclobutanecarboxylic acid {(S)-3-[3-(4-bromo-benzyl)-2,4-dioxo-1,3,8-triaza-spiro[4.5]dec-8-yl]-1-phenyl-propyl}-amide hydrochloride Compound 21 4,4-Difluoro-cyclohexanecarboxylic acid {(S)-3-[3-(4-bromo-benzyl)-2,4-dioxo-1,3,8-triaza-spiro[4.5]dec-8-yl]-1-phenyl-propyl}-amide hydrochloride Compound 22 Tetrahydro-pyran-4-carboxylic acid {(S)-3-[3-(4-bromo-benzyl)-2,4-dioxo-1,3,8-triaza-spiro[4.5]dec-8-yl]-1-phenyl-propyl}-amide hydrochloride Compound 23 N-{(S)-3-[3-(4-Methoxy-benzyl)-2,4-dioxo-1,3,8-triaza-spiro[4.5]dec-8-yl]-1-phenyl-propyl}-benzamide hydrochloride Compound 24 N-{(S)-3-[3-(4-Methoxy-benzyl)-2,4-dioxo-1,3,8-triaza-spiro[4.5]dec-8-yl]-1-phenyl-propyl}-2-phenyl-acetamide hydrochloride Compound 25 N-{(S)-3-[3-(4-Methoxy-benzyl)-2,4-dioxo-1,3,8-triaza-spiro[4.5]dec-8-yl]-1-phenyl-propyl}-nicotinamide hydrochloride Compound 26 N-{(S)-3-[3-(4-Methoxy-benzyl)-2,4-dioxo-1,3,8-triaza-spiro[4.5]dec-8-yl]-1-phenyl-propyl}-acetamide hydrochloride Compound 27 N-{(S)-3-[3-(4-Methoxy-benzyl)-2,4-dioxo-1,3,8-triaza-spiro[4.5]dec-8-yl]-1-phenyl-propyl}-propionamide hydrochloride Compound 28 N-{(S)-3-[3-(4-Methoxy-benzyl)-2,4-dioxo-1,3,8-triaza-spiro[4.5]dec-8-yl]-1-phenyl-propyl}-isobutyramide hydrochloride Compound 29 N-{(S)-3-[3-(4-Methoxy-benzyl)-2,4-dioxo-1,3,8-triaza-spiro[4.5]dec-8-yl]-1-phenyl-propyl}-2,2-dimethyl-propionamide hydrochloride Compound 30 1-Methyl-cyclopropanecarboxylic acid {(S)-3-[3-(4-methoxy-benzyl)-2,4-dioxo-1,3,8-triaza-spiro[4.5]dec-8-yl]-1-phenyl-propyl}-amide hydrochloride Compound 31 2-Cyclopropyl-N-{(S)-3-[3-(4-methoxy-benzyl)-2,4-dioxo-1,3,8-triaza-spiro[4.5]dec-8-yl]-1-phenyl-propyl}-acetamide hydrochloride Compound 32 Cyclobutanecarboxylic acid {(S)-3-[3-(4-methoxy-benzyl)-2,4-dioxo-1,3,8-triaza-spiro[4.5]dec-8-yl]-1-phenyl-propyl}-amide hydrochloride Compound 33 Cyclohexanecarboxylic acid {(S)-3-[3-(4-methoxy-benzyl)-2,4-dioxo-1,3,8-triaza-spiro[4.5]dec-8-yl]-1-phenyl-propyl}-amide hydrochloride Compound 34 4,4-Difluoro-cyclohexanecarboxylic acid {(S)-3-[3-(4-methoxy-benzyl)-2,4-dioxo-1,3,8-triaza-spiro[4.5]dec-8-yl]-1-phenyl-propyl}-amide hydrochloride Compound 35 Tetrahydro-pyran-4-carboxylic acid {(S)-3-[3-(4-methoxy-benzyl)-2,4-dioxo-1,3,8-triaza-spiro[4.5]dec-8-yl]-1-phenyl-propyl}-amide hydrochloride Compound 36 N-{(S)-3-[3-(4-Methanesulfonyl-benzyl)-2,4-dioxo-1,3,8-triaza-spiro[4.5]dec-8-yl]-1-phenyl-propyl}-benzamide hydrochloride Compound 37 N-{(S)-3-[3-(4-Methanesulfonyl-benzyl)-2,4-dioxo-1,3,8-triaza-spiro[4.5]dec-8-yl]-1-phenyl-propyl}-2-phenyl-acetamide hydrochloride Compound 38 N-{(S)-3-[3-(4-Methanesulfonyl-benzyl)-2,4-dioxo-1,3,8-triaza-spiro[4.5]dec-8-yl]-1-phenyl-propyl}-nicotinamide hydrochloride Compound 39 N-{(S)-3-[3-(4-Methanesulfonyl-benzyl)-2,4-dioxo-1,3,8-triaza-spiro[4.5]dec-8-yl]-1-phenyl-propyl}-acetamide hydrochloride Compound 40 N-{(S)-3-[3-(4-Methanesulfonyl-benzyl)-2,4-dioxo-1,3,8-triaza-spiro[4.5]dec-8-yl]-1-phenyl-propyl}-propionamide hydrochloride Compound 41 N-{(S)-3-[3-(4-Methanesulfonyl-benzyl)-2,4-dioxo-1,3,8-triaza-spiro[4.5]dec-8-yl]-1-phenyl-propyl}-isobutyramide hydrochloride Compound 42 N-{(S)-3-[3-(4-Methanesulfonyl-benzyl)-2,4-dioxo-1,3,8-triaza-spiro[4.5]dec-8-yl]-1-phenyl-propyl}-2,2-dimethyl-propionamide hydrochloride Compound 43 Cyclopropanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 44 1-Methyl-cyclopropanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 45 2-Cyclopropyl-N-{(S)-3-[3-(4-methanesulfonyl-benzyl)-2,4-dioxo-1,3,8-triaza-spiro[4.5]dec-8-yl]-1-phenyl-propyl}-acetamide hydrochloride Compound 46 Cyclobutanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 47 Cyclopentanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 48 Cyclohexanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 49 4,4-Difluoro-cyclohexanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 50 Tetrahydro-pyran-4-carboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 51 N-{(S)-3-[3-(4-Methoxy-benzyl)-1-methyl-2,4-dioxo-1,3,8-triaza-spiro[4.5]dec-8-yl]-1-phenyl-propyl}-isobutyramide hydrochloride Compound 52 Cyclopropanecarboxylic acid {(S)-3-[3-(4-methoxy-benzyl)-1-methyl-2,4-dioxo-1,3,8-triaza-spiro[4.5]dec-8-yl]-1-phenyl-propyl}-amide hydrochloride Compound 53 4,4-Difluoro-cyclohexanecarboxylic acid {(S)-3-[3-(4-methoxy-benzyl)-1-methyl-2,4-dioxo-1,3,8-triaza-spiro[4.5]dec-8-yl]-1-phenyl-propyl}-amide hydrochloride Compound 54 N-{(S)-3-[3-(4-Fluoro-benzyl)-2,4-dioxo-1,3,8-triaza-spiro[4.5]dec-8-yl]-1-phenyl-propyl}-isobutyramide hydrochloride Compound 55 N-{(S)-3-[3-(4-Chloro-benzyl)-2,4-dioxo-1,3,8-triaza-spiro[4.5]dec-8-yl]-1-phenyl-propyl}-isobutyramide hydrochloride Compound 56 N-{(S)-3-[3-(4-Cyano-benzyl)-2,4-dioxo-1,3,8-triaza-spiro[4.5]dec-8-yl]-1-phenyl-propyl}-isobutyramide hydrochloride Compound 57 N-{(S)-3-[2,4-Dioxo-3-(4-trifluoromethyl-benzyl)-1,3,8-triaza-spiro[4.5]dec-8-yl]-1-phenyl-propyl}-isobutyramide hydrochloride Compound 58 N-{(S)-3-[2,4-Dioxo-3-(4-trifluoromethoxy-benzyl)-1,3,8-triaza-spiro[4.5]dec-8-yl]-1-phenyl-propyl}-isobutyramide hydrochloride Compound 59 N-{(S)-3-[2,4-Dioxo-3-(4-pyrazol-1-yl-benzyl)-1,3,8-triaza-spiro[4.5]dec-8-yl]-1-phenyl-propyl}-isobutyramide hydrochloride Compound 60 Cyclopropanecarboxylic acid {(S)-3-[3-(4-fluoro-benzyl)-2,4-dioxo-1,3,8-triaza-spiro[4.5]dec-8-yl]-1-phenyl-propyl}-amide hydrochloride Compound 61 Cyclopropanecarboxylic acid {(S)-3-[3-(4-chloro-benzyl)-2,4-dioxo-1,3,8-triaza-spiro[4.5]dec-8-yl]-1-phenyl-propyl}-amide hydrochloride Compound 62 Cyclopropanecarboxylic acid {(S)-3-[3-(4-cyano-benzyl)-2,4-dioxo-1,3,8-triaza-spiro[4.5]dec-8-yl]-1-phenyl-propyl}-amide hydrochloride Compound 63 Cyclopropanecarboxylic acid {(S)-3-[3-(4-difluoromethoxy-benzyl)-2,4-dioxo-1,3,8-triaza-spiro[4.5]dec-8-yl]-1-phenyl-propyl}-amide hydrochloride Compound 64 Cyclopropanecarboxylic acid {(S)-3-[2,4-dioxo-3-(4-trifluoromethyl-benzyl)-1,3,8-triaza-spiro[4.5]dec-8-yl]-1-phenyl-propyl}-amide hydrochloride Compound 65 Cyclopropanecarboxylic acid {(S)-3-[2,4-dioxo-3-(4-trifluoromethoxy-benzyl)-1,3,8-triaza-spiro[4.5]dec-8-yl]-1-phenyl-propyl}-amide hydrochloride Compound 66 Cyclopropanecarboxylic acid {(S)-3-[2,4-dioxo-3-(4-pyrazol-1-yl-benzyl)-1,3,8-triaza-spiro[4.5]dec-8-yl]-1-phenyl-propyl}-amide hydrochloride Compound 67 Morpholine-4-carboxylic acid {(S)-3-[3-(4-bromo-benzyl)-2,4-dioxo-1,3,8-triaza-spiro[4.5]dec-8-yl]-1-phenyl-propyl}-amide hydrochloride Compound 68 Pyrrolidine-1-carboxylic acid {(S)-3-[3-(4-bromo-benzyl)-2,4-dioxo-1,3,8-triaza-spiro[4.5]dec-8-yl]-1-phenyl-propyl}-amide hydrochloride Compound 69 3,3-Difluoro-pyrrolidine-1-carboxylic acid {(S)-3-[3-(4-bromo-benzyl)-2,4-dioxo-1,3,8-triaza-spiro[4.5]dec-8-yl]-1-phenyl-propyl}-amide hydrochloride Compound 70 3-{(S)-3-[3-(4-Bromo-benzyl)-2,4-dioxo-1,3,8-triaza-spiro[4.5]dec-8-yl]-1-phenyl-propyl}-1,1-dimethyl-urea hydrochloride Compound 71 1-{(S)-3-[3-(4-Bromo-benzyl)-2,4-dioxo-1,3,8-triaza-spiro[4.5]dec-8-yl]-1-phenyl-propyl}-3-cyclopentyl-urea hydrochloride Compound 72 Morpholine-4-carboxylic acid {(S)-3-[3-(4-methoxy-benzyl)-2,4-dioxo-1,3,8-triaza-spiro[4.5]dec-8-yl]-1-phenyl-propyl}-amide hydrochloride Compound 73 Pyrrolidine-1-carboxylic acid {(S)-3-[3-(4-methoxy-benzyl)-2,4-dioxo-1,3,8-triaza-spiro[4.5]dec-8-yl]-1-phenyl-propyl}-amide hydrochloride Compound 74 3,3-Difluoro-pyrrolidine-1-carboxylic acid {(S)-3-[3-(4-methoxy-benzyl)-2,4-dioxo-1,3,8-triaza-spiro[4.5]dec-8-yl]-1-phenyl-propyl}-amide hydrochloride Compound 75 3-{(S)-3-[3-(4-Methoxy-benzyl)-2,4-dioxo-1,3,8-triaza-spiro[4.5]dec-8-yl]-1-phenyl-propyl}-1,1-dimethyl-urea hydrochloride Compound 76 1-Cyclopentyl-3-{(S)-3-[3-(4-methoxy-benzyl)-2,4-dioxo-1,3,8-triaza-spiro[4.5]dec-8-yl]-1-phenyl-propyl}-urea hydrochloride Compound 77 Morpholine-4-carboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 78 Pyrrolidine-1-carboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 79 3,3-Difluoro-pyrrolidine-1-carboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride Compound 80 3-{(S)-3-[3-(4-Methanesulfonyl-benzyl)-2,4-dioxo-1,3,8-triaza-spiro[4.5]dec-8-yl]-1-phenyl-propyl}-1,1-dimethyl-urea hydrochloride Compound 81 1-Cyclopentyl-3-{(S)-3-[3-(4-methanesulfonyl-benzyl)-2,4-dioxo-1,3,8-triaza-spiro[4.5]dec-8-yl]-1-phenyl-propyl}-urea hydrochloride Compound 82 {(S)-3-[3-(4-Bromo-benzyl)-2,4-dioxo-1,3,8-triaza-spiro[4.5]dec-8-yl]-1-phenyl-propyl}-carbamic acid methyl ester hydrochloride Compound 83 {(S)-3-[3-(4-Bromo-benzyl)-2,4-dioxo-1,3,8-triaza-spiro[4.5]dec-8-yl]-1-phenyl-propyl}-carbamic acid ethyl ester hydrochloride Compound 84 {(S)-3-[3-(4-Bromo-benzyl)-2,4-dioxo-1,3,8-triaza-spiro[4.5]dec-8-yl]-1-phenyl-propyl}-carbamic acid isopropyl ester hydrochloride Compound 85 {(S)-3-[3-(4-Bromo-benzyl)-2,4-dioxo-1,3,8-triaza-spiro[4.5]dec-8-yl]-1-phenyl-propyl}-carbamic acid cyclopentyl ester hydrochloride Compound 86 {(S)-3-[3-(4-Methoxy-benzyl)-2,4-dioxo-1,3,8-triaza-spiro[4.5]dec-8-yl]-1-phenyl-propyl}-carbamic acid methyl ester hydrochloride Compound 87 {(S)-3-[3-(4-Methoxy-benzyl)-2,4-dioxo-1,3,8-triaza-spiro[4.5]dec-8-yl]-1-phenyl-propyl}-carbamic acid ethyl ester hydrochloride
Compound 88 {(S)-3-[3-(4-Methoxy-benzyl)-2,4-dioxo-1,3,8-triaza-spiro[4.5]dec-8-yl]-1-phenyl-propyl}-carbamic acid isopropyl ester hydrochloride
Compound 89 {(S)-3-[3-(4-Methoxy-benzyl)-2,4-dioxo-1,3,8-triaza-spiro[4.5]dec-8-yl]-1-phenyl-propyl}-carbamic acid cyclopentyl ester hydrochloride
Compound 90 {(S)-3-[3-(4-Methanesulfonyl-benzyl)-2,4-dioxo-1,3,8-triaza-spiro[4.5]dec-8-yl]-1-phenyl-propyl}-carbamic acid methyl ester hydrochloride
Compound 91 {(S)-3-[3-(4-Methanesulfonyl-benzyl)-2,4-dioxo-1,3,8-triaza-spiro[4.5]dec-8-yl]-1-phenyl-propyl}-carbamic acid ethyl ester hydrochloride
Compound 92 {(S)-3-[3-(4-Methanesulfonyl-benzyl)-2,4-dioxo-1,3,8-triaza-spiro[4.5]dec-8-yl]-1-phenyl-propyl}-carbamic acid isopropyl ester hydrochloride
Compound 93 {(S)-3-[3-(4-Methanesulfonyl-benzyl)-2,4-dioxo-1,3,8-triaza-spiro[4.5]dec-8-yl]-1-phenyl-propyl}-carbamic acid cyclopentyl ester hydrochloride
Compound 94 Ethanesulfonic acid {(S)-3-[3-(4-bromo-benzyl)-2,4-dioxo-1,3,8-triaza-spiro[4.5]dec-8-yl]-1-phenyl-propyl}-amide hydrochloride
Compound 95 Cyclopropanesulfonic acid {(S)-3-[3-(4-bromo-benzyl)-2,4-dioxo-1,3,8-triaza-spiro[4.5]dec-8-yl]-1-phenyl-propyl}-amide hydrochloride
Compound 96 Ethanesulfonic acid {(S)-3-[3-(4-methoxy-benzyl)-2,4-dioxo-1,3,8-triaza-spiro[4.5]dec-8-yl]-1-phenyl-propyl}-amide hydrochloride
Compound 97 Cyclopropanesulfonic acid {(S)-3-[3-(4-methoxy-benzyl)-2,4-dioxo-1,3,8-triaza-spiro[4.5]dec-8-yl]-1-phenyl-propyl}-amide hydrochloride
Compound 98 Ethanesulfonic acid {(S)-3-[3-(4-methanesulfonyl-benzyl)-2,4-dioxo-1,3,8-triaza-spiro[4.5]dec-8-yl]-1-phenyl-propyl}-amide hydrochloride
Compound 99 Cyclopropanesulfonic acid {(S)-3-[3-(4-methanesulfonyl-benzyl)-2,4-dioxo-1,3,8-triaza-spiro[4.5]dec-8-yl]-1-phenyl-propyl}-amide hydrochloride
Compound 100 N-{(S)-3-[3-(4-Bromo-benzyl)-1-methyl-2,4-dioxo-1,3,8-triaza-spiro[4.5]dec-8-yl]-1-phenyl-propyl}-isobutyramide hydrochloride
Compound 101 N-{(S)-3-[3-(4-Bromo-benzyl)-1-ethyl-2,4-dioxo-1,3,8-triaza-spiro[4.5]dec-8-yl]-1-phenyl-propyl}-isobutyramide hydrochloride
Compound 102 N-{(S)-3-[1-Allyl-3-(4-bromo-benzyl)-2,4-dioxo-1,3,8-triaza-spiro[4.5]dec-8-yl]-1-phenyl-propyl}-isobutyramide hydrochloride
Compound 103 N-{(S)-3-[3-(4-Bromo-benzyl)-1-isopropyl-2,4-dioxo-1,3,8-triaza-spiro[4.5]dec-8-yl]-1-phenyl-propyl}-isobutyramide hydrochloride
Compound 104 N-{(S)-3-[3-(4-Bromo-benzyl)-2,4-dioxo-1-phenyl-1,3,8-triaza-spiro[4.5]dec-8-yl]-1-phenyl-propyl}-isobutyramide hydrochloride
Compound 105 N-{(S)-3-[1-Benzyl-3-(4-bromo-benzyl)-2,4-dioxo-1,3,8-triaza-spiro[4.5]dec-8-yl]-1-phenyl-propyl}-isobutyramide hydrochloride
Compound 106 Cyclopropanecarboxylic acid {(S)-3-[3-(4-bromo-benzyl)-1-methyl-2,4-dioxo-1,3,8-triaza-spiro[4.5]dec-8-yl]-1-phenyl-propyl}-amide hydrochloride
Compound 107 Cyclopropanecarboxylic acid {(S)-3-[3-(4-bromo-benzyl)-1-ethyl-2,4-dioxo-1,3,8-triaza-spiro[4.5]dec-8-yl]-1-phenyl-propyl}-amide hydrochloride
Compound 108 Cyclopropanecarboxylic acid {(S)-3-[1-allyl-3-(4-bromo-benzyl)-2,4-dioxo-1,3,8-triaza-spiro[4.5]dec-8-yl]-1-phenyl-propyl}-amide hydrochloride
Compound 109 Cyclopropanecarboxylic acid {(S)-3-[3-(4-bromo-benzyl)-1-isopropyl-2,4-dioxo-1,3,8-triaza-spiro[4.5]dec-8-yl]-1-phenyl-propyl}-amide hydrochloride
Compound 110 Cyclopropanecarboxylic acid {(S)-3-[3-(4-bromo-benzyl)-2,4-dioxo-1-phenyl-1,3,8-triaza-spiro[4.5]dec-8-yl]-1-phenyl-propyl}-amide hydrochloride
Compound 111 Cyclopropanecarboxylic acid {(S)-3-[1-benzyl-3-(4-bromo-benzyl)-2,4-dioxo-1,3,8-triaza-spiro[4.5]dec-8-yl]-1-phenyl-propyl}-amide hydrochloride
Compound 112 4,4-Difluoro-cyclohexanecarboxylic acid {(S)-3-[3-(4-bromo-benzyl)-1-methyl-2,4-dioxo-1,3,8-triaza-spiro[4.5]dec-8-yl]-1-phenyl-propyl}-amide hydrochloride
Compound 113 4,4-Difluoro-cyclohexanecarboxylic acid {(S)-3-[3-(4-bromo-benzyl)-1-ethyl-2,4-dioxo-1,3,8-triaza-spiro[4.5]dec-8-yl]-1-phenyl-propyl}-amide hydrochloride
Compound 114 4,4-Difluoro-cyclohexanecarboxylic acid {(S)-3-[1-allyl-3-(4-bromo-benzyl)-2,4-dioxo-1,3,8-triaza-spiro[4.5]dec-8-yl]-1-phenyl-propyl}-amide hydrochloride
Compound 115 4,4-Difluoro-cyclohexanecarboxylic acid {(S)-3-[3-(4-bromo-benzyl)-1-isopropyl-2,4-dioxo-1,3,8-triaza-spiro[4.5]dec-8-yl]-1-phenyl-propyl}-amide hydrochloride
Compound 116 4,4-Difluoro-cyclohexanecarboxylic acid {(S)-3-[3-(4-bromo-benzyl)-2,4-dioxo-1-phenyl-1,3,8-triaza-spiro[4.5]dec-8-yl]-1-phenyl-propyl}-amide hydrochloride
Compound 117 4,4-Difluoro-cyclohexanecarboxylic acid {(S)-3-[1-benzyl-3-(4-bromo-benzyl)-2,4-dioxo-1,3,8-triaza-spiro[4.5]dec-8-yl]-1-phenyl-propyl}-amide hydrochloride or pharmaceutically acceptable salts, hydrates or solvates thereof.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 μM, preferably about 2 to 50 μM, most preferably about 3 to about 30 μM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

When the compound (I) or a pharmaceutically acceptable salt, hydrate or solvate thereof is used in combination with a second therapeutic active agent, the dose of each compound may be either the same as or different from that when the compound is used alone. Conventional doses and regimens are readily appreciated by those skilled in the art, including doses described in the Physicians Desk Reference, $56^{th}$ edition, 2002.

The present invention is directed to the use of the compounds as modulators of CCR5 chemokine receptor activity. In particular, the compounds of the invention have been found to have activity in binding to the CCR5 receptor in the biological assay, as described in Example 8, generally with an $IC_{50}$ value of less than 25 µM. The terms "modulator" or "modulation" are meant to include antagonism, agonism, mixed and partial antagonism and agonism.

Certain compounds of the presents invention have also been tested in an assay for HIV activity, as described in Example 5, and generally having an $IC_{50}$ value of less than 1 µM.

The purity and mass of the following examples were characterized by mass spectra (LC/MS) and/or NMR spectra.

The following general schemes and examples are provided to illustrate various embodiments of the present invention and shall not be considered as limiting in scope.

The entire disclosure of all applications, patents and publications, cited above and below, and of U.S. Provisional Application No. 60/501,420, filed Sep. 10, 2003 is hereby incorporated by reference.

In the foregoing and in the following examples, all temperatures are set forth uncorrected in degrees Celsius; and, unless otherwise indicated, all parts and percentages are by weight. (Note: yields are by weight but chromatographic conditions are by volume)

EXAMPLES

The following abbreviations may be used as follows:
br broad
DCE 1,2-dichloroethane
DCM dichloromethane
DMF N,N-dimethylformamide
Hal halogen
Sept. septuplet
TFA trifluoroacetic acid
Semi-preparative HPLC purification procedures:
Column: Phenomenex Luna $C_{18}(2)$, 5 microns, 10×250 mm
Buffer A: 3 mM HCl in $H_2O$ (pH 2.4-2.6)
Buffer B: acetonitrile
Method A: 0-60% B in 50 min. (1.2%/min)
Method B: 15-60% B in 32 min. (1.4%/min)
Method C: 0-25% B in 25 min. (1%/min)
Method D: 15-40% B in 25 min. (1%/min)

Scheme 1

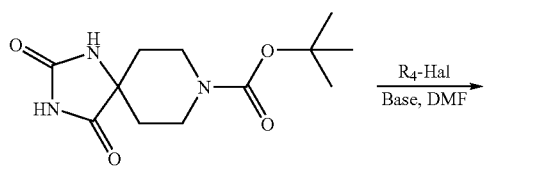

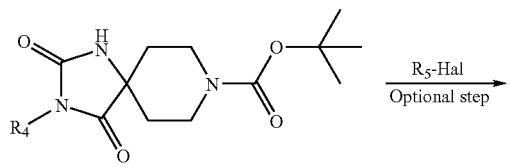

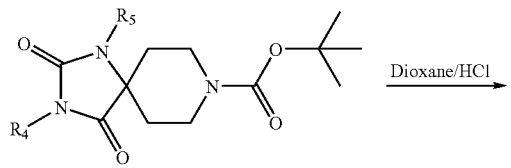

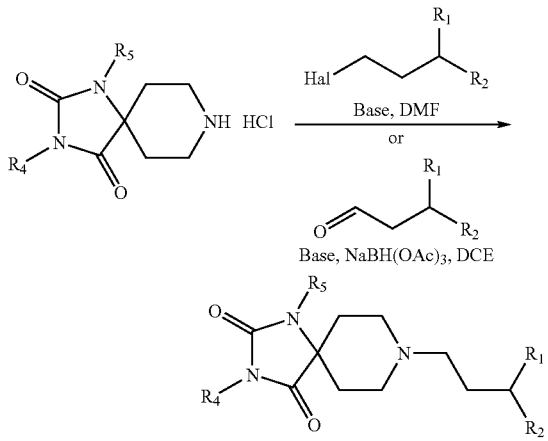

Preparation 1

3-(4-Methoxybenzyl)-2,4-dioxo-1,3,8-triazaspiro[4.5]decane-8-carboxylic acid tert-butyl ester

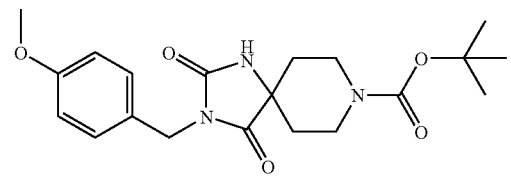

To 1 g (3.7 mmol) of 2,4-dioxo-1,3,8-triaza-spiro[4.5]decane-8-carboxylic acid tert-butyl ester were added successively 554 µL (4.08 mmol) of 4-methoxybenzyl chloride, 565 mg (4.08 mmol) of potassium carbonate and 37 mL of anhydrous DMF. The reaction mixture was stirred overnight at room temperature. Then 250 mL of water were added and a white precipitated solid was collected by filtration. This crude material was back washed with diethyl ether and dried under reduced pressure yielding 1.15 g (79%) of 3-(4-methoxybenzyl)-2,4-dioxo-1,3,8-triazaspiro[4.5]decane-8-carboxylic acid tert-butyl ester as a white solid.

$^1$H NMR (400 MHz, $CD_2Cl_2$): δ [ppm] 7.27 (d, 2H), 6.85 (d, 2H), 6.16 (s, 1H), 4.57 (s, 2H), 3.96 (m, 2H), 3.78 (s, 3H), 3.17 (m, 2H), 1.95 (m, 2H), 1.58 (m, 2H), 1.45 (s, 9H).

Preparation 2

3-(4-Methoxybenzyl)-1,3,8-triaza-spiro[4.5]decane-2,4-dione hydrochloride

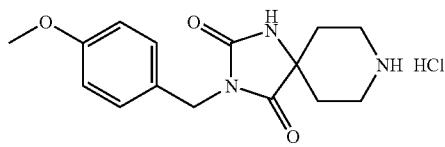

To 1.15 g (2.95 mmol) of 3-(4-methoxybenzyl)-2,4-dioxo-1,3,8-triazaspiro[4.5]decane-8-carboxylic acid tert-butyl ester was added 8 mL of dioxan and 6 mL of 4N solution of dioxane/HCl. The reaction mixture was stirred for 2 hours at room temperature and concentrated in vacuo. The crude was dissolved in a minimum of methanol and diethyl ether was added to obtain, after filtration, the 3-(4-methoxybenzyl)-1,3,8-triaza-spiro[4.5]decane-2,4-dione hydrochloride as a white solid (644 mg, 67%).

$^1$H NMR (400 MHz, DMSO-$d_6$): δ [ppm] 9.22 (br s, 1H), 9.05 (s, 1H), 8.89 (br s, 1H), 7.16 (d, 2H), 6.87 (d, 2H), 4.44 (s, 2H), 3.71 (s, 3H), 3.29 (m, 2H), 3.13 (m, 2H), 2.06 (m, 2H), 1.77 (br d, 2H).

Preparation 3

3-(4-Bromo-benzyl)-2,4-dioxo-1,3,8-triaza-spiro[4.5]decane-8-carboxylic acid tert-butyl ester

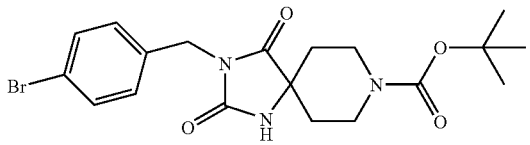

This spirohydantoin compound was prepared as described in preparation 1, starting from 2.5 g (9.28 mmol) of 2,4-dioxo-1,3,8-triaza-spiro[4.5]decane-8-carboxylic acid tert-butyl ester yielding 3.27 g (80.5%) of 3-(4-bromo-benzyl)-2,4-dioxo-1,3,8-triaza-spiro[4.5]decane-8-carboxylic acid tert-butyl ester as a colorless solid.

$^1$H NMR (400 MHz, DMSO-$d_6$): δ [ppm] 8.93 (s, 1H), 7.50 (d, 2H), 7.16 (d, 2H), 4.47 (s, 2H), 3.78 (d, 2H), 3.11 (br s, 2H), 1.69 (m, 2H), 1.52 (m, 2H), 1.37 (s, 9H).

Preparation 4

3-(4-Bromo-benzyl)-1,3,8-triaza-spiro[4.5]decane-2,4-dione hydrochloride

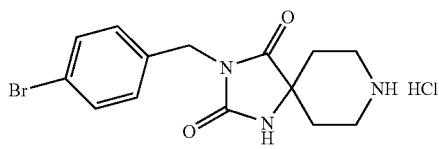

As described in preparation 2, 2.5 g (5.7 mmol) of 3-(4-bromo-benzyl)-2,4-dioxo-1,3,8-triaza-spiro[4.5]decane-8-carboxylic acid tert-butyl ester was deprotected under acidic conditions giving access to 1.85 g (86.8%) of 3-(4-bromo-benzyl)-1,3,8-triaza-spiro[4.5]decane-2,4-dione hydrochloride as a white solid.

$^1$H NMR (400 MHz, DMSO-$d_6$): δ [ppm] 9.27 (br s, 1H), 9.10 (s, 1H), 8.94 (br s, 1H), 7.49 (d, 2H), 7.17 (d, 2H), 4.47 (s, 2H), 3.29 (m, 2H), 3.11 (m, 2H), 2.06 (m, 2H), 1.80 (br d, 2H).

Preparation 5

3-(4-Methoxy-benzyl)-1-methyl-2,4-dioxo-1,3,8-triaza-spiro[4.5]decane-8-carboxylic acid tert-butyl ester

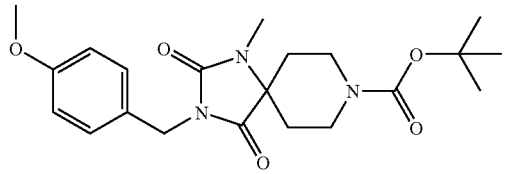

390 mg (1 mmol) of 3-(4-methoxybenzyl)-2,4-dioxo-1,3,8-triazaspiro[4.5]decane-8-carboxylic acid tert-butyl ester were solubilized in 5 mL of DMF under nitrogen before adding 61 mg (1.5 mmol) of sodium hydride in mineral oil 60%. The reaction mixture was agitated for 5 minutes before the addition of 70 μL (1.1 mmol) of iodomethane. After 2 hours of agitation at room temperature, the reaction mixture was quenched with 20 mL of water and then extracted with diethyl ether (2×20 mL). The organic layers were dried over sodium sulfate, filtrated and evaporated in vacuo to give quantitatively (404 mg) 3-(4-methoxy-benzyl)-1-methyl-2,4-dioxo-1,3,8-triaza-spiro[4.5]decane-8-carboxylic acid tert-butyl ester as a yellowish oil.

$^1$H NMR (400 MHz, DMSO-$d_6$): δ [ppm] 7.14 (d, 2H), 6.85 (d, 2H), 4.44 (s, 2H), 3.91 (br s, 2H), 3.69 (s, 3H), 3.27 (br s, 2H), 2.73 (s, 3H), 1.82 (m, 2H), 1.58 (d, 2H), 1.38 (s, 9H).

Preparation 6

3-(4-Methoxy-benzyl)-1-methyl-1,3,8-triaza-spiro[4.5]decane-2,4-dione hydrochloride

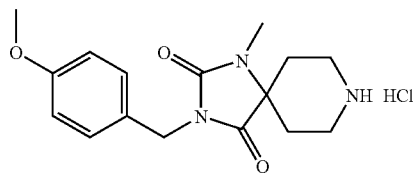

403 mg (1 mmol) of 3-(4-methoxy-benzyl)-1-methyl-2,4-dioxo-1,3,8-triaza-spiro[4.5]decane-8-carboxylic acid tert-butyl ester were dissolved in a minimum of diethyl ether before adding 3 mL of a solution of dioxane/HCl 4N. The reaction mixture was agitated 10 minutes at room temperature and then evaporated. The yellow crude was triturated with diethyl ether and filtered to yield 115.3 mg (34%) of 3-(4-methoxy-benzyl)-1-methyl-1,3,8-triaza-spiro[4.5]decane-2,4-dione hydrochloride as a pale yellow solid.

$^1$H NMR (400 MHz, DMSO-$d_6$): δ [ppm] 9.14 (br s, 2H), 7.15 (d, 2H), 6.85 (d, 2H), 4.45 (s, 2H), 3.69 (s, 3H), 3.30 (br s, 4H), 2.74 (s, 3H), 2.30 (m, 2H), 1.80 (d, 2H).

Example 1

3-(4-Bromobenzyl)-8-(3,3-diphenyl-propyl)-1,3,8-triaza-spiro[4.5]decane-2,4-dione hydrochloride (Compound 3)

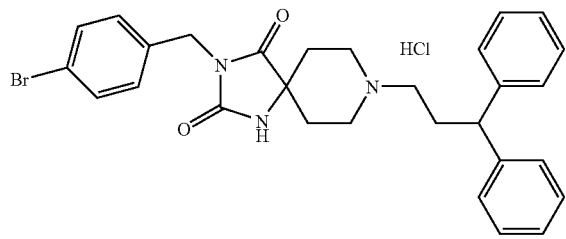

A mixture of 26.2 mg (70 μmol) of 3-(4-bromo-benzyl)-1,3,8-triaza-spiro[4.5]decane-2,4-dione hydrochloride, 21.4 mg (70 μmol) of 3,3-diphenylpropyl bromide and 29 mg (210 μmol) of potassium carbonate in 1 mL of anhydrous DMF was heated overnight at 60° C. After cooling to room temperature, 0.5 mL of water was added and the solution was extracted with DCM (2×2 mL). The crude material was purified by semi-preparative HPLC (method A) yielding 12.8 mg (32.1%) of Compound 3 as a white solid.

$^1$H NMR (400 MHz, DMSO-d$_6$): δ [ppm] 10.21 (br s, 1H), 8.98 (s, 1H), 7.49 (d, 2H), 7.32-7.27 (m, 8H), 7.18 (m, 4H), 4.47 (s, 2H), 4.0 (t, 1H), 3.56 (br d, 1H), 3.28 (m, 3H), 3.02 (q, 2H), 2.84 (m, 1H), 2.16 (t, 2H), 2.0 (m, 1H), 1.83 (br d, 2H).

Table 1 of compounds illustrates some of the compounds of the present invention which were synthesized using the procedures described in scheme 1.

TABLE 1

| CPD | STRUCTURE | COMPOUND NAME | MOLWT | PURITY |
|---|---|---|---|---|
| 1 | 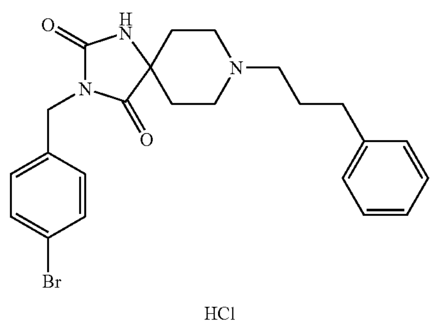 | 3-(4-Bromobenzyl)-8-(3-phenyl-propyl)-1,3,8-triaza-spiro[4.5]decane-2,4-dione hydrochloride | 492.842 | 90+ (HPLC) |
| 2 | 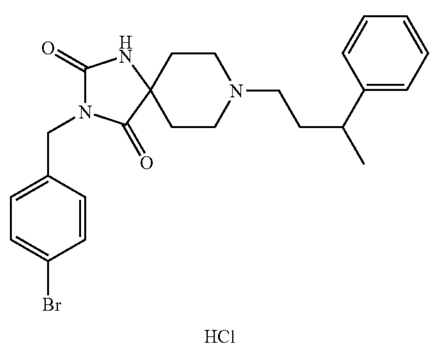 | 3-(4-Bromobenzyl)-8-(3-phenyl-butyl)-1,3,8-triaza-spiro[4.5]decane-2,4-dione hydrochloride | 506.869 | 90+ (HPLC) |
| 3 | 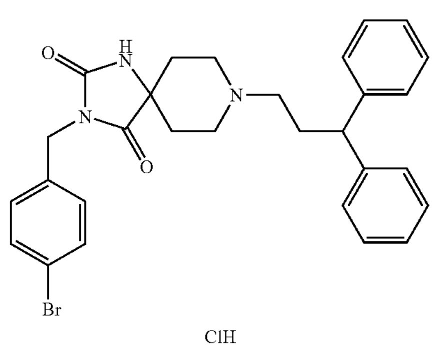 | 3-(4-Bromobenzyl)-8-(3,3-diphenyl-propyl)-1,3,8-triaza-spiro[4.5]decane-2,4-dione hydrochloride | 568.94 | 92.2% (HPLC) |

Scheme 2

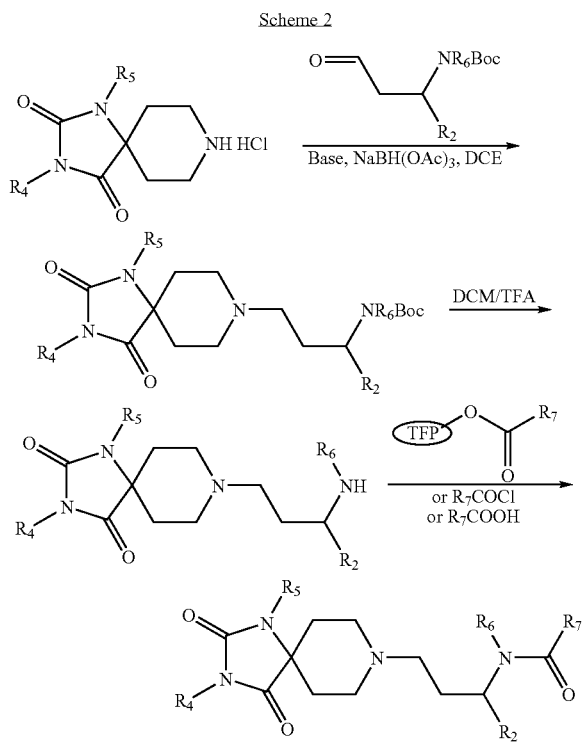

Example 2

{3-[3-(4-Bromobenzyl)-2,4-dioxo-1,3,8-triaza-spiro[4.5dec-8-yl]-1-(S)-phenylpropyl}-carbamic acid tert-butyl ester (Compound 4)

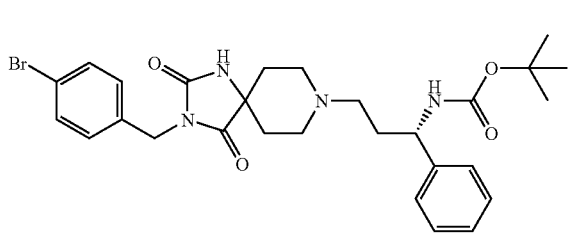

To a solution of 115 mg (0.307 mmol) of 3-(4-bromobenzyl)-1,3,8-triaza-spiro[4.5]decane-2,4-dione hydrochloride in 5 mL of anhydrous DCE were added successively 76.6 mg (0.307 mmol) of (3-oxo-1-(S)-phenylpropyl)-carbamic acid tert-butyl ester and 50 μL (0.358 mmol) of triethylamine. The reaction mixture was agitated at room temperature for 10 minutes before adding 85 mg (0.382 mmol) of sodium triacetoxyborohydride. After an overnight agitation, 10 mL of saturated solution of sodium bicarbonate were added. Then the solution was extracted with DCM, dried over sodium sulfate, filtered and concentrated in vacuo. The crude was purified by flash chromatography on bond elute silica gel eluting with 20% ethanol/ethyl acetate and Compound 4, as a colorless solid, was obtained (133 mg, 75.8%).

$^1$H NMR (400 MHz, CDCl$_3$): δ [ppm] 7.44 (d, 2H), 7.36-7.2 (m, 7H), 6.06 (br s, 1H), 4.85-4.7 (m, 1H), 4.58 (m, 2H), 3.0-2.8 (m, 2H), 2.5-1.5 (m, 10H), 1.42 (s, 9H). LC/MS: m/z 572.52 (MH$^+$).

Example 3

8-(3-(S)-Amino-3-phenylpropyl)-3-(4-bromobenzyl)-1,3,8-triaza-spiro[4.5]decane-2,4-dione (Compound 5)

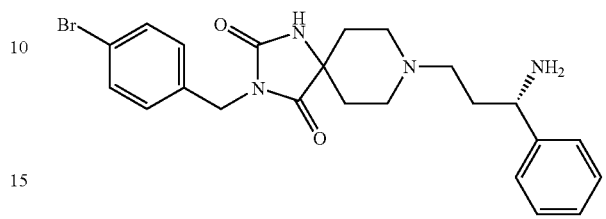

To 116 mg (0.2 mmol) of {3-[3-(4-bromobenzyl)-2,4-dioxo-1,3,8-triaza-spiro[4.5]dec-8-yl]-1-(S)-phenylpropyl}-carbamic acid tert-butyl ester were added 2 mL of a solution DCM/TFA 20%. The reaction mixture was agitated one hour at room temperature before neutralizing with 1.8 mL of a 10% aqueous solution of sodium hydroxide. Then the solution was extracted with DCM, dried over sodium sulfate, filtered and evaporated in vacuo yielding Compound 5 as a white solid (97 mg, 100%).

$^1$H NMR (400 MHz, CDCl$_3$): δ [ppm] 7.43 (d, 2H), 7.36-7.2 (m, 7H), 6.32 (s, 1H), 4.57 (s, 2H), 4.05-3.95 (m, 1H), 3.0-2.8 (m, 2H), 2.5-2.3 (m, 2H), 2.2-1.5 (m, 12H).

Example 4

N-{3-[3-(4-Bromobenzyl)-2,4-dioxo-1,3,8-triaza-spiro[4.5]dec-8-yl]-1-(S)-phenylpropyl}-isobutyramide hydrochloride (Compound 6)

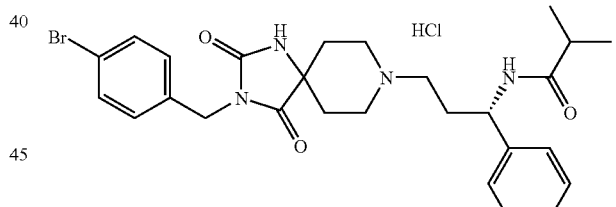

To 100 mg (100 μmol, loading of 1 mmol/g) of isopropylcarboxyl activated ester on polymeric 4-hydroxy-2,3,5,6-tetrafluorobenzamido (TFP) resin (see preparation in J. M. Salvino et al. *J. Comb. Chem.* 2000, 2, 691-697), preswollen with 0.5 mL of anhydrous DMF, was added 28.2 mg (60 μmol) of 8-(3-(S)-amino-3-phenylpropyl)-3-(4-bromobenzyl)-1,3,8-triaza-spiro[4.5]decane-2,4-dione diluted in 1 mL of DMF. The reaction was agitated overnight at room temperature. The mixture was filtered and washed with DCM (2×2 mL). The washes were collected and evaporated in vacuo. The crude was purified by semi-preparative HPLC (method B) and 16.8 mg (48.4%) of Compound 6 as a colorless solid was isolated.

$^1$H NMR (400 MHz, DMSO-d$_6$): δ [ppm] 10.37 (br s, 1H), 9.12 (s, 1H), 8.34 (d, 1H), 7.51 (d, 2H), 7.35 (m, 4H), 7.24 (m, 1H), 7.19 (d, 2H), 4.88 (m, 1H), 4.5 (s, 2H), 3.52 (m, 2H), 3.15-2.9 (m, 4H), 2.45 (sept., 1H), 2.25-2.1 (m, 4H), 1.85 (br d, 2H), 1.03 (d, 3H), 0.97 (d, 3H).

Table 2 of compounds illustrates some of the compounds of the present invention which were synthesized using the procedures described in scheme 2.

TABLE 2

| CPD | STRUCTURE | COMPOUND NAME | MOLWT | PURITY |
|---|---|---|---|---|
| 4 | 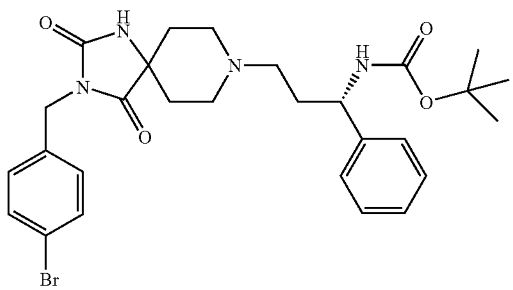 | {3-[3-(4-Bromo-benzyl)-2,4-dioxo-1,3,8-triaza-spiro[4.5]dec-8-yl]-1-(S)-phenyl-propyl}-carbamic acid tert-butyl ester | 571.513 | 99.9% (HPLC) |
| 5 | 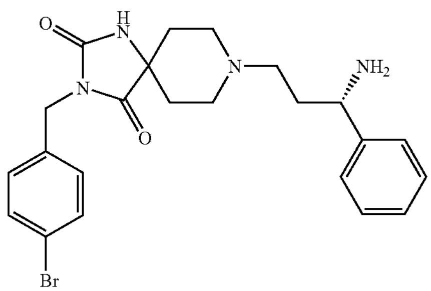 | 8-(3-(S)-Amino-3-phenyl-propyl)-3-(4-bromo-benzyl)-1,3,8-triaza-spiro[4.5]decane-2,4-dione | 471.396 | >95% (1H NMR) |
| 6 | 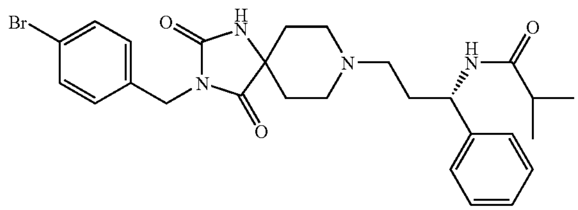 | (S)-3-(4-Bromobenzyl)-8-(3-isobutyrylamino-3-phenyl-propyl)-2,4-dioxo-1,3,8-triaza-spiro[4.5]decane hydrochloride | 577.948 | 98+ (LC/MS) |
| 7 | 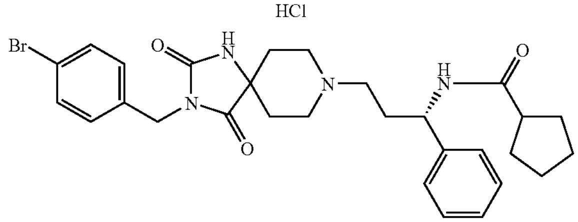 | (S)-3-(4-Bromobenzyl)-8-[3-(cyclopentanecarbonyl-amino)-3-phenyl-propyl]-2,4-dioxo-1,3,8-triaza-spiro[4.5]decane hydrochloride | 603.985 | 98+ (LC/MS) |
| 8 | 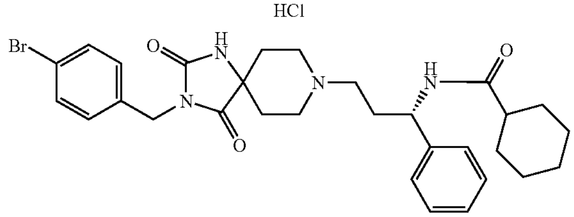 | (S)-3-(4-Bromobenzyl)-8-[3-(cyclohexanecarbonyl-amino)-3-phenyl-propyl]-2,4-dioxo-1,3,8-triaza-spiro[4.5]decane hydrochloride | 618.012 | 98+ (LC/MS) |

TABLE 2-continued

| CPD | STRUCTURE | COMPOUND NAME | MOLWT | PURITY |
|---|---|---|---|---|
| 9 | HCl | Cyclopentanecarboxylic acid {3-(S)-[3-(4-methoxy-benzyl)-2,4-dioxo-1,3,8-triaza-spiro[4.5]dec-8-yl]-1-phenyl-propyl}-amide hydrochloride | 555.115 | 98+ (LC/MS) |
| 10 | HCl | Cyclopropanecarboxylic acid {3-(S)-[3-(4-methoxy-benzyl)-2,4-dioxo-1,3,8-triaza-spiro[4.5]dec-8-yl]-1-phenyl-propyl}-amide hydrochloride | 527.062 | 98+ (LC/MS) |

Table 2a of compounds illustrates some additional compounds of the present invention which were synthesized using the procedures described in scheme 2.

TABLE 2a

| CPD | STRUCTURE | COMPOUND NAME | MOLWT | PURITY |
|---|---|---|---|---|
| 11 | HCl | N-{(S)-3-[3-(4-Bromo-benzyl)-2,4-dioxo-1,3,8-triaza-spiro[4.5]dec-8-yl]-1-phenyl-propyl}-benzamide hydrochloride | 611.97 | 99+ (HPLC) |
| 12 | HCl | N-{(S)-3-[3-(4-Bromo-benzyl)-2,4-dioxo-1,3,8-triaza-spiro[4.5]dec-8-yl]-1-phenyl-propyl}-2-phenyl-acetamide hydrochloride | 626 | 99+ (HPLC) |

TABLE 2a-continued

| CPD | STRUCTURE | COMPOUND NAME | MOLWT | PURITY |
|---|---|---|---|---|
| 13 | HCl | N-{(S)-3-[3-(4-Bromo-benzyl)-2,4-dioxo-1,3,8-triaza-spiro[4.5]dec-8-yl]-1-phenyl-propyl}-nicotinamide hydrochloride | 612.96 | 99+ (HPLC) |
| 14 | HCl | N-{(S)-3-[3-(4-Bromo-benzyl)-2,4-dioxo-1,3,8-triaza-spiro[4.5]dec-8-yl]-1-phenyl-propyl}-acetamide hydrochloride | 549.9 | 99+ (HPLC) |
| 15 | HCl | N-{(S)-3-[3-(4-Bromo-benzyl)-2,4-dioxo-1,3,8-triaza-spiro[4.5]dec-8-yl]-1-phenyl-propyl}-propionamide hydrochloride | 563.93 | 99+ (HPLC) |
| 16 | HCl | N-{(S)-3-[3-(4-Bromo-benzyl)-2,4-dioxo-1,3,8-triaza-spiro[4.5]dec-8-yl]-1-phenyl-propyl}-2,2-dimethyl-propionamide hydrochloride | 591.98 | 99+ (HPLC) |
| 17 | HCl | Cyclopropanecarboxylic acid {(S)-3-[3-(4-bromo-benzyl)-2,4-dioxo-1,3,8-triaza-spiro[4.5]dec-8-yl]-1-phenyl-propyl}-amide hydrochloride | 575.94 | 99+ (HPLC) |

TABLE 2a-continued

| CPD | STRUCTURE | COMPOUND NAME | MOLWT | PURITY |
|---|---|---|---|---|
| 18 | HCl | 1-Methyl-cyclopropanecarboxylic acid {(S)-3-[3-(4-bromo-benzyl)-2,4-dioxo-1,3,8-triaza-spiro[4.5]dec-8-yl]-1-phenyl-propyl}-amide hydrochloride | 589.96 | 99+ (HPLC) |
| 19 | HCl | N-{(S)-3-[3-(4-Bromo-benzyl)-2,4-dioxo-1,3,8-triaza-spiro[4.5]dec-8-yl]-1-phenyl-propyl}-2-cyclopropyl-acetamide hydrochloride | 589.96 | 99+ (HPLC) |
| 20 | HCl | Cyclobutanecarboxylic acid {(S)-3-[3-(4-bromo-benzyl)-2,4-dioxo-1,3,8-triaza-spiro[4.5]dec-8-yl]-1-phenyl-propyl}-amide hydrochloride | 589.96 | 99+ (HPLC) |
| 21 | HCl | 4,4-Difluoro-cyclohexanecarboxylic acid {(S)-3-[3-(4-bromo-benzyl)-2,4-dioxo-1,3,8-triaza-spiro[4.5]dec-8-yl]-1-phenyl-propyl}-amide hydrochloride | 654 | 99+ (HPLC) |
| 22 | HCl | Tetrahydro-pyran-4-carboxylic acid {(S)-3-[3-(4-bromo-benzyl)-2,4-dioxo-1,3,8-triaza-spiro[4.5]dec-8-yl]-1-phenyl-propyl}-amide hydrochloride | 619.99 | 99+ (HPLC) |

TABLE 2a-continued

| CPD | STRUCTURE | COMPOUND NAME | MOLWT | PURITY |
|---|---|---|---|---|
| 23 | HCl 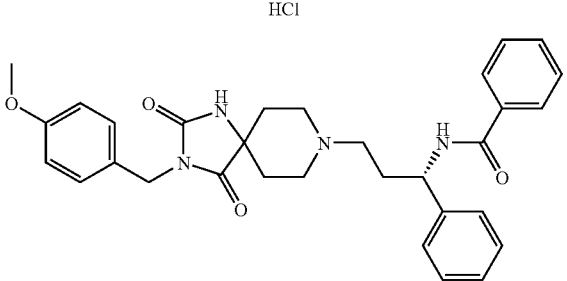 | N-{(S)-3-[3-(4-Methoxy-benzyl)-2,4-dioxo-1,3,8-triaza-spiro[4.5]dec-8-yl]-1-phenyl-propyl}-benzamide hydrochloride | 611.97 | 99+ (HPLC) |
| 24 | HCl 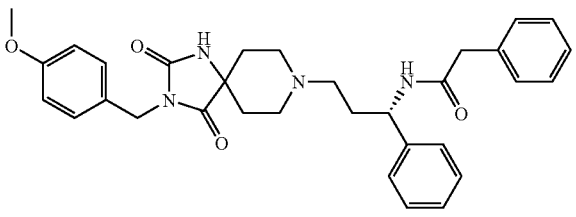 | N-{(S)-3-[3-(4-Methoxy-benzyl)-2,4-dioxo-1,3,8-triaza-spiro[4.5]dec-8-yl]-1-phenyl-propyl}-2-phenyl-acetamide hydrochloride | 577.13 | 99+ (HPLC) |
| 25 | HCl 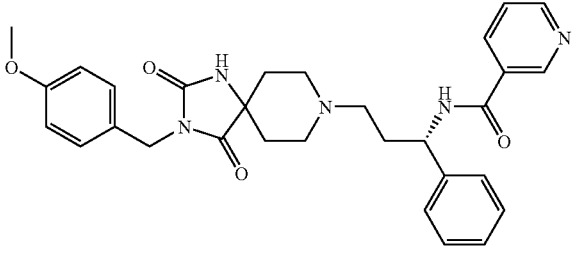 | N-{(S)-3-[3-(4-Methoxy-benzyl)-2,4-dioxo-1,3,8-triaza-spiro[4.5]dec-8-yl]-1-phenyl-propyl}-nicotinamide hydrochloride | 564.09 | 99+ (HPLC) |
| 26 | HCl 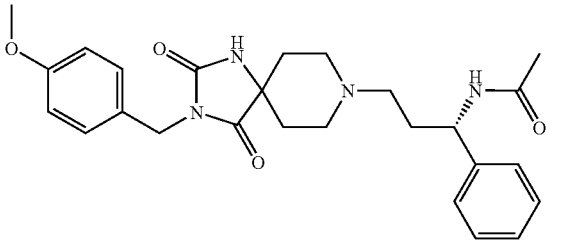 | N-{(S)-3-[3-(4-Methoxy-benzyl)-2,4-dioxo-1,3,8-triaza-spiro[4.5]dec-8-yl]-1-phenyl-propyl}-acetamide hydrochloride | 501.03 | 98+ (HPLC) |
| 27 | HCl 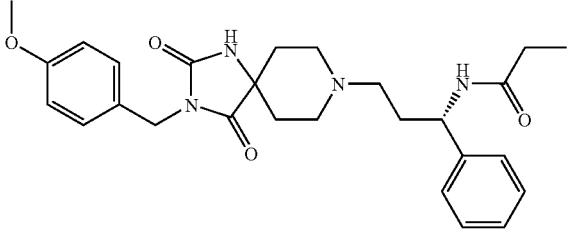 | N-{(S)-3-[3-(4-Methoxy-benzyl)-2,4-dioxo-1,3,8-triaza-spiro[4.5]dec-8-yl]-1-phenyl-propyl}-propionamide hydrochloride | 515.06 | 99+ (HPLC) |

TABLE 2a-continued

| CPD | STRUCTURE | COMPOUND NAME | MOLWT | PURITY |
|---|---|---|---|---|
| 28 | HCl | N-{(S)-3-[3-(4-Methoxy-benzyl)-2,4-dioxo-1,3,8-triaza-spiro[4.5]dec-8-yl]-1-phenyl-propyl}-isobutyramide hydrochloride | 529.08 | 98+ (HPLC) |
| 29 | HCl | N-{(S)-3-[3-(4-Methoxy-benzyl)-2,4-dioxo-1,3,8-triaza-spiro[4.5]dec-8-yl]-1-phenyl-propyl}-2,2-dimethyl-propionamide hydrochloride | 543.11 | 99+ (HPLC) |
| 30 | HCl | 1-Methyl-cyclopropanecarboxylic acid {(S)-3-[3-(4-methoxy-benzyl)-2,4-dioxo-1,3,8-triaza-spiro[4.5]dec-8-yl]-1-phenyl-propyl}-amide hydrochloride | 541.09 | 99+ (HPLC) |
| 31 | HCl | 2-Cyclopropyl-N-{(S)-3-[3-(4-methoxy-benzyl)-2,4-dioxo-1,3,8-triaza-spiro[4.5]dec-8-yl]-1-phenyl-propyl}-acetamide hydrochloride | 541.09 | 99+ (HPLC) |
| 32 | HCl | Cyclobutanecarboxylic acid {(S)-3-[3-(4-methoxy-benzyl)-2,4-dioxo-1,3,8-triaza-spiro[4.5]dec-8-yl]-1-phenyl-propyl}-amide hydrochloride | 541.09 | 99+ (HPLC) |

TABLE 2a-continued

| CPD | STRUCTURE | COMPOUND NAME | MOLWT | PURITY |
|---|---|---|---|---|
| 33 | HCl | Cyclohexanecarboxylic acid {(S)-3-[3-(4-methoxy-benzyl)-2,4-dioxo-1,3,8-triaza-spiro[4.5]dec-8-yl]-1-phenyl-propyl}-amide hydrochloride | 569.15 | 99+ (HPLC) |
| 34 | HCl | 4,4-Difluoro-cyclohexanecarboxylic acid {(S)-3-[3-(4-methoxy-benzyl)-2,4-dioxo-1,3,8-triaza-spiro[4.5]dec-8-yl]-1-phenyl-propyl}-amide hydrochloride | 605.13 | 98+ (HPLC) |
| 35 | HCl | Tetrahydro-pyran-4-carboxylic acid {(S)-3-[3-(4-methoxy-benzyl)-2,4-dioxo-1,3,8-triaza-spiro[4.5]dec-8-yl]-1-phenyl-propyl}-amide hydrochloride | 571.12 | 99+ (HPLC) |
| 36 | HCl | N-{(S)-3-[3-(4-Methanesulfonyl-benzyl)-2,4-dioxo-1,3,8-triaza-spiro[4.5]dec-8-yl]-1-phenyl-propyl}-benzamide hydrochloride | 611.16 | 99+ (HPLC) |
| 37 | HCl | N-{(S)-3-[3-(4-Methanesulfonyl-benzyl)-2,4-dioxo-1,3,8-triaza-spiro[4.5]dec-8-yl]-1-phenyl-propyl}-2-phenyl-acetamide hydrochloride | 625.19 | 99+ (HPLC) |

TABLE 2a-continued

| CPD | STRUCTURE | COMPOUND NAME | MOLWT | PURITY |
|---|---|---|---|---|
| 38 | HCl | N-{(S)-3-[3-(4-Methanesulfonyl-benzyl)-2,4-dioxo-1,3,8-triaza-spiro[4.5]dec-8-yl]-1-phenyl-propyl}-nicotinamide hydrochloride | 612.15 | 99+ (HPLC) |
| 39 | HCl | N-{(S)-3-[3-(4-Methanesulfonyl-benzyl)-2,4-dioxo-1,3,8-triaza-spiro[4.5]dec-8-yl]-1-phenyl-propyl}-acetamide hydrochloride | 549.09 | 99+ (HPLC) |
| 40 | HCl | N-{(S)-3-[3-(4-Methanesulfonyl-benzyl)-2,4-dioxo-1,3,8-triaza-spiro[4.5]dec-8-yl]-1-phenyl-propyl}-propionamide hydrochloride | 563.12 | 99+ (HPLC) |
| 41 | HCl | N-{(S)-3-[3-(4-Methanesulfonyl-benzyl)-2,4-dioxo-1,3,8-triaza-spiro[4.5]dec-8-yl]-1-phenyl-propyl}-isobutyramide hydrochloride | 577.15 | 98+ (HPLC) |
| 42 | HCl | N-{(S)-3-[3-(4-Methanesulfonyl-benzyl)-2,4-dioxo-1,3,8-triaza-spiro[4.5]dec-8-yl]-1-phenyl-propyl}-2,2-dimethyl-propionamide hydrochloride | 591.17 | 99+ (HPLC) |

TABLE 2a-continued

| CPD | STRUCTURE | COMPOUND NAME | MOLWT | PURITY |
|---|---|---|---|---|
| 43 | HCl | Cyclopropanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 575.13 | 99+ (HPLC) |
| 44 | HCl | 1-Methyl-cyclopropanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 589.16 | 99+ (HPLC) |
| 45 | HCl | 2-Cyclopropyl-N-{(S)-3-[3-(4-methanesulfonyl-benzyl)-2,4-dioxo-1,3,8-triaza-spiro[4.5]dec-8-yl]-1-phenyl-propyl}-acetamide hydrochloride | 589.16 | 99+ (HPLC) |
| 46 | HCl | Cyclobutanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 589.16 | 98+ (HPLC) |
| 47 | HCl | Cyclopentanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 603.19 | 99+ (HPLC) |

TABLE 2a-continued

| CPD | STRUCTURE | COMPOUND NAME | MOLWT | PURITY |
|---|---|---|---|---|
| 48 | HCl | Cyclohexanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 617.21 | 99+ (HPLC) |
| 49 | HCl | 4,4-Difluoro-cyclohexanecarboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 653.19 | 99+ (HPLC) |
| 50 | HCl | Tetrahydro-pyran-4-carboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 619.18 | 99+ (HPLC) |
| 51 | HCl | N-{(S)-3-[3-(4-Methoxy-benzyl)-1-methyl-2,4-dioxo-1,3,8-triaza-spiro[4.5]dec-8-yl]-1-phenyl-propyl}-isobutyramide hydrochloride | 543.11 | 99+ (HPLC) |
| 52 | HCl | Cyclopropanecarboxylic acid {(S)-3-[3-(4-methoxy-benzyl)-1-methyl-2,4-dioxo-1,3,8-triaza-spiro[4.5]dec-8-yl]-1-phenyl-propyl}-amide hydrochloride | 541.09 | 99+ (HPLC) |

TABLE 2a-continued

| CPD | STRUCTURE | COMPOUND NAME | MOLWT | PURITY |
|---|---|---|---|---|
| 53 | HCl | 4,4-Difluoro-cyclohexanecarboxylic acid {(S)-3-[3-(4-methoxy-benzyl)-1-methyl-2,4-dioxo-1,3,8-triaza-spiro[4.5]dec-8-yl]-1-phenyl-propyl}-amide hydrochloride | 619.16 | 98+ (HPLC) |
| 54 | HCl | N-{(S)-3-[3-(4-Fluoro-benzyl)-2,4-dioxo-1,3,8-triaza-spiro[4.5]dec-8-yl]-1-phenyl-propyl}-isobutyramide hydrochloride | 517.05 | 94+ (HPLC) |
| 55 | HCl | N-{(S)-3-[3-(4-Chloro-benzyl)-2,4-dioxo-1,3,8-triaza-spiro[4.5]dec-8-yl]-1-phenyl-propyl}-isobutyramide hydrochloride | 533.5 | 95+ (HPLC) |
| 56 | HCl | N-{(S)-3-[3-(4-Cyano-benzyl)-2,4-dioxo-1,3,8-triaza-spiro[4.5]dec-8-yl]-1-phenyl-propyl}-isobutyramide hydrochloride | 524.07 | 94+ (HPLC) |
| 57 | HCl | N-{(S)-3-[2,4-Dioxo-3-(4-trifluoromethyl-benzyl)-1,3,8-triaza-spiro[4.5]dec-8-yl]-1-phenyl-propyl}-isobutyramide hydrochloride | 567.06 | 97+ (HPLC) |

TABLE 2a-continued

| CPD | STRUCTURE | COMPOUND NAME | MOLWT | PURITY |
|---|---|---|---|---|
| 58 | HCl | N-{(S)-3-[2,4-Dioxo-3-(4-trifluoromethoxy-benzyl)-1,3,8-triaza-spiro[4.5]dec-8-yl]-1-phenyl-propyl}-isobutyramide hydrochloride | 583.05 | 98+ (HPLC) |
| 59 | HCl | N-{(S)-3-[2,4-Dioxo-3-(4-pyrazol-1-yl-benzyl)-1,3,8-triaza-spiro[4.5]dec-8-yl]-1-phenyl-propyl}-isobutyramide hydrochloride | 565.12 | 98+ (HPLC) |
| 60 | HCl | Cyclopropanecarboxylic acid {(S)-3-[3-(4-fluoro-benzyl)-2,4-dioxo-1,3,8-triaza-spiro[4.5]dec-8-yl]-1-phenyl-propyl}-amide hydrochloride | 515.03 | 98+ (HPLC) |
| 61 | HCl | Cyclopropanecarboxylic acid {(S)-3-[3-(4-chloro-benzyl)-2,4-dioxo-1,3,8-triaza-spiro[4.5]dec-8-yl]-1-phenyl-propyl}-amide hydrochloride | 531.49 | 98+ (HPLC) |
| 62 | HCl | Cyclopropanecarboxylic acid {(S)-3-[3-(4-cyano-benzyl)-2,4-dioxo-1,3,8-triaza-spiro[4.5]dec-8-yl]-1-phenyl-propyl}-amide hydrochloride | 522.05 | 98+ (HPLC) |

TABLE 2a-continued

| CPD | STRUCTURE | COMPOUND NAME | MOLWT | PURITY |
|---|---|---|---|---|
| 63 | 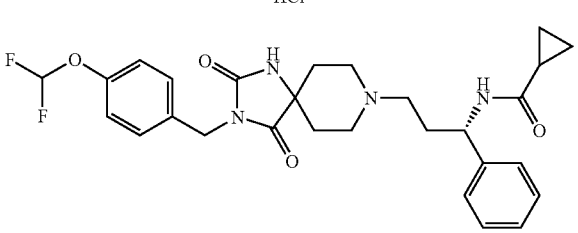 HCl | Cyclopropanecarboxylic acid {(S)-3-[3-(4-difluoromethoxy-benzyl)-2,4-dioxo-1,3,8-triaza-spiro[4.5]dec-8-yl]-1-phenyl-propyl}-amide hydrochloride | 563.05 | 98+ (HPLC) |
| 64 | 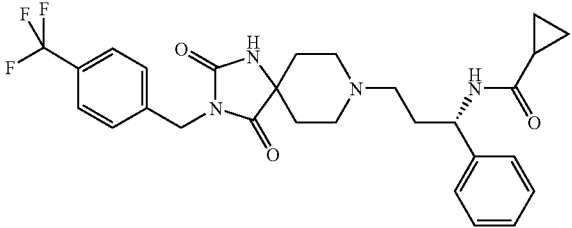 HCl | Cyclopropanecarboxylic acid {(S)-3-[2,4-dioxo-3-(4-trifluoromethyl-benzyl)-1,3,8-triaza-spiro[4.5]dec-8-yl]-1-phenyl-propyl}-amide hydrochloride | 565.04 | 96+ (HPLC) |
| 65 | 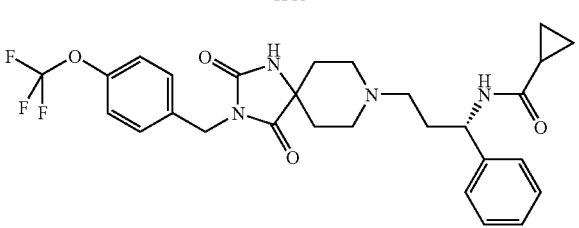 HCl | Cyclopropanecarboxylic acid {(S)-3-[2,4-dioxo-3-(4-trifluoromethoxy-benzyl)-1,3,8-triaza-spiro[4.5]dec-8-yl]-1-phenyl-propyl}-amide hydrochloride | 581.04 | 94+ (HPLC) |
| 66 | 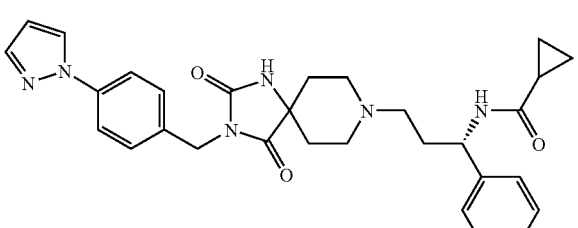 HCl | Cyclopropanecarboxylic acid {(S)-3-[2,4-dioxo-3-(4-pyrazol-1-yl-benzyl)-1,3,8-triaza-spiro[4.5]dec-8-yl]-1-phenyl-propyl}-amide hydrochloride | 563.1 | 99+ (HPLC) |

Scheme 3

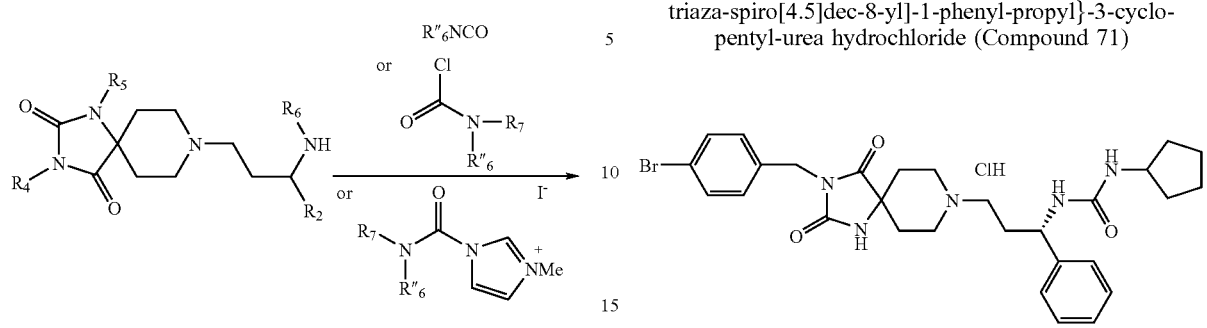

Example 5

1-{(S)-3-[3-(4-Bromo-benzyl)-2,4-dioxo-1,3,8-triaza-spiro[4.5]dec-8-yl]-1-phenyl-propyl}-3-cyclopentyl-urea hydrochloride (Compound 71)

To a solution of 8-(3-(S)-amino-3-phenylpropyl)-3-(4-bromobenzyl)-1,3,8-triaza-spiro[4.5]decane-2,4-dione (60 μmol) in THF (1 mL) was added a solution of cyclopentyl isocyanate (72 μmol) in THF. The reaction mixture was agitated overnight at room temperature and then concentrated in vacuo. The residue was purified by semi-preparative HPLC (Method C) and lyophilized to give Compound 71 as a colorless solid (18.8 mg, 51%).

$^1$H NMR (400 MHz, DMSO-d$_6$): δ [ppm] 10.42 (br d, 1H), 8.93 (br d, 1H), 7.49 (d, 2H), 7.35-7.22 (m, 5H), 7.17 (d, 2H), 6.43 (d, 1H), 6.0 (d, 1H), 4.78-4.68 (m, 1H), 4.48 (s, 2H), 3.83-3.78 (m, 1H), 3.55-3.30 (m, 2H), 3.19-2.96 (m, 4H), 2.23-2.0 (m, 4H), 1.83 (d, 2H), 1.80-1.67 (m, 2H), 1.62-1.40 (m, 4H), 1.30-1.18 (m, 2H).

Table 3 of compounds illustrates some of the compounds of the present invention which were synthesized using the procedures described in scheme 3.

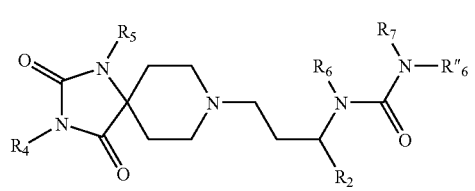

TABLE 3

| CPD | STRUCTURE | COMPOUND NAME | MOLWT | PURITY |
|---|---|---|---|---|
| 67 | HCl | Morpholine-4-carboxylic acid {(S)-3-[3-(4-bromo-benzyl)-2,4-dioxo-1,3,8-triaza-spiro[4.5]dec-8-yl]-1-phenyl-propyl}-amide hydrochloride | 620.98 | 99+ (HPLC) |
| 68 | HCl | Pyrrolidine-1-carboxylic acid {(S)-3-[3-(4-bromo-benzyl)-2,4-dioxo-1,3,8-triaza-spiro[4.5]dec-8-yl]-1-phenyl-propyl}-amide hydrochloride | 604.98 | 99+ (HPLC) |

TABLE 3-continued

| CPD | STRUCTURE | COMPOUND NAME | MOLWT | PURITY |
|---|---|---|---|---|
| 69 | HCl | 3,3-Difluoro-pyrrolidine-1-carboxylic acid {(S)-3-[3-(4-bromo-benzyl)-2,4-dioxo-1,3,8-triaza-spiro[4.5]dec-8-yl]-1-phenyl-propyl}-amide hydrochloride | 640.96 | 99+ (HPLC) |
| 70 | HCl | 3-{(S)-3-[3-(4-Bromo-benzyl)-2,4-dioxo-1,3,8-triaza-spiro[4.5]dec-8-yl]-1-phenyl-propyl}-1,1-dimethyl-urea hydrochloride | 578.94 | 99+ (HPLC) |
| 71 | HCl | 1-{(S)-3-[3-(4-Bromo-benzyl)-2,4-dioxo-1,3,8-triaza-spiro[4.5]dec-8-yl]-1-phenyl-propyl}-3-cyclopentyl-urea hydrochloride | 619.01 | 99+ (HPLC) |
| 72 | HCl | Morpholine-4-carboxylic acid {(S)-3-[3-(4-methoxy-benzyl)-2,4-dioxo-1,3,8-triaza-spiro[4.5]dec-8-yl]-1-phenyl-propyl}-amide hydrochloride | 572.11 | 97+ (HPLC) |
| 73 | HCl | Pyrrolidine-1-carboxylic acid {(S)-3-[3-(4-methoxy-benzyl)-2,4-dioxo-1,3,8-triaza-spiro[4.5]dec-8-yl]-1-phenyl-propyl}-amide hydrochloride | 556.11 | 99+ (HPLC) |

TABLE 3-continued

| CPD | STRUCTURE | COMPOUND NAME | MOLWT | PURITY |
|---|---|---|---|---|
| 74 | HCl | 3,3-Difluoro-pyrrolidine-1-carboxylic acid {(S)-3-[3-(4-methoxy-benzyl)-2,4-dioxo-1,3,8-triaza-spiro[4.5]dec-8-yl]-1-phenyl-propyl}-amide hydrochloride | 592.09 | 99+ (HPLC) |
| 75 | HCl | 3-{(S)-3-[3-(4-Methoxy-benzyl)-2,4-dioxo-1,3,8-triaza-spiro[4.5]dec-8-yl]-1-phenyl-propyl}-1,1-dimethyl-urea hydrochloride | 530.07 | 99+ (HPLC) |
| 76 | HCl | 1-Cyclopentyl-3-{(S)-3-[3-(4-methoxy-benzyl)-2,4-dioxo-1,3,8-triaza-spiro[4.5]dec-8-yl]-1-phenyl-propyl}-urea hydrochloride | 570.14 | 99+ (HPLC) |
| 77 | HCl | Morpholine-4-carboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 620.17 | 99+ (HPLC) |
| 78 | HCl | Pyrrolidine-1-carboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 604.17 | 97+ (HPLC) |

TABLE 3-continued

| CPD | STRUCTURE | COMPOUND NAME | MOLWT | PURITY |
|---|---|---|---|---|
| 79 | HCl | 3,3-Difluoro-pyrrolidine-1-carboxylic acid {(S)-3-[3-(4-methanesulfonyl-benzyl)-2,4-dioxo-1,3,8-triaza-spiro[4.5]dec-8-yl]-1-phenyl-propyl}-amide hydrochloride | 640.15 | 99+ (HPLC) |
| 80 | HCl | 3-{(S)-3-[3-(4-Methanesulfonyl-benzyl)-2,4-dioxo-1,3,8-triaza-spiro[4.5]dec-8-yl]-1-phenyl-propyl}-1,1-dimethyl-urea hydrochloride | 578.13 | 99+ (HPLC) |
| 81 | HCl | 1-Cyclopentyl-3-{(S)-3-[3-(4-methanesulfonyl-benzyl)-2,4-dioxo-1,3,8-triaza-spiro[4.5]dec-8-yl]-1-phenyl-propyl}-urea hydrochloride | 618.2 | 99+ (HPLC) |

Example 6

{(S)-3-[3-(4-Bromo-benzyl)-2,4-dioxo-1,3,8-triaza-spiro[4.5]dec-8-yl]-1-phenyl-propyl}-carbamic acid methyl ester hydrochloride (Compound 82)

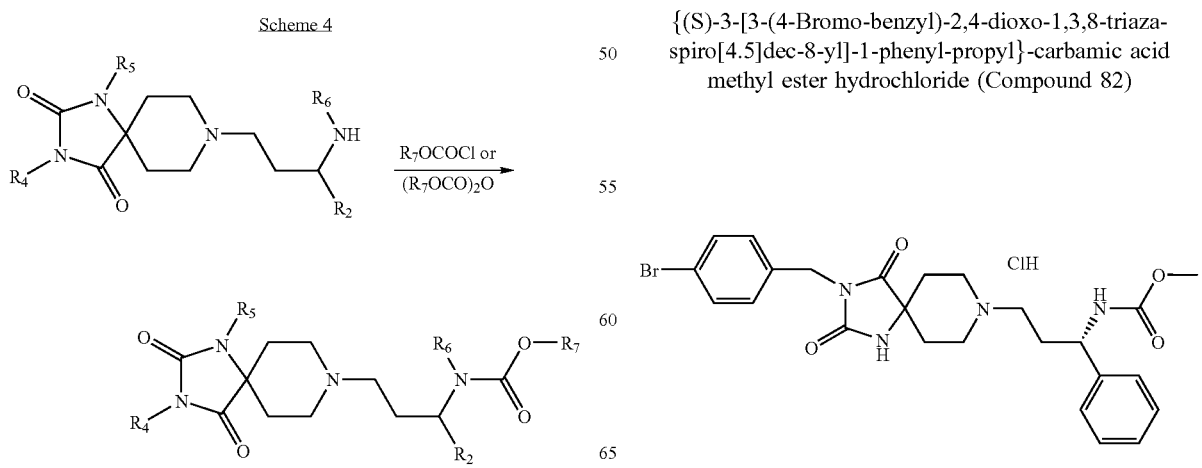

To a solution of 8-(3-(S)-amino-3-phenylpropyl)-3-(4-bromobenzyl)-1,3,8-triaza-spiro[4.5]decane-2,4-dione (60 μmol) in anhydrous DCE (1 mL) was added triethylamine (10 μL, 72 μmol) and a solution of methyl chloroformate (72 μmol) in anhydrous DCE. The reaction mixture was agitated overnight at room temperature and then concentrated in vacuo. The residue was purified by semi-preparative HPLC (Method D) and lyophilized to give Compound 82 as a colorless solid (14.1 mg, 42%).

$^1$H NMR (400 MHz, DMSO-d$_6$): δ [ppm] 10.57 (br d, 1H), 8.91 (br d, 1H), 7.85 (d, 1H), 7.49 (d, 2H), 7.38-7.22 (m, 5H), 7.17 (d, 2H), 4.63-4.53 (m, 1H), 4.48 (s, 2H), 3.50 (s, 3H), 3.53-3.40 (m, 2H), 3.19-2.98 (m, 4H), 2.30-2.0 (m, 4H), 1.83 (d, 2H).

Table 4 of compounds illustrates some of the compounds of the present invention which were synthesized using the procedures described in scheme 4.

TABLE 4

| CPD | STRUCTURE | COMPOUND NAME | MOLWT | PURITY |
|---|---|---|---|---|
| 82 | 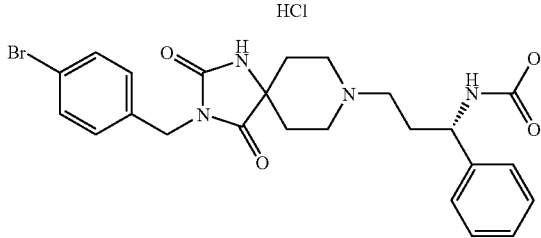 HCl | {(S)-3-[3-(4-Bromo-benzyl)-2,4-dioxo-1,3,8-triaza-spiro[4.5]dec-8-yl]-1-phenyl-propyl}-carbamic acid methyl ester hydrochloride | 565.9 | 97+ (HPLC) |
| 83 | 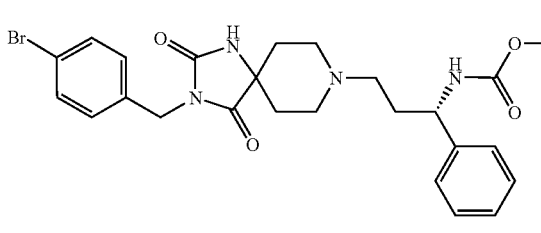 HCl | {(S)-3-[3-(4-Bromo-benzyl)-2,4-dioxo-1,3,8-triaza-spiro[4.5]dec-8-yl]-1-phenyl-propyl}-carbamic acid ethyl ester hydrochloride | 579.93 | 99+ (HPLC) |
| 84 | 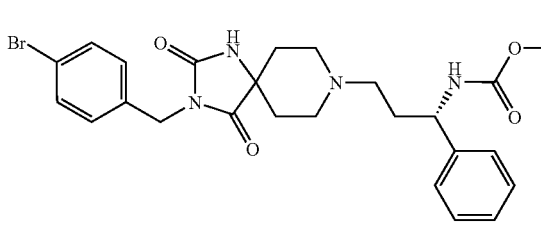 HCl | {(S)-3-[3-(4-Bromo-benzyl)-2,4-dioxo-1,3,8-triaza-spiro[4.5]dec-8-yl]-1-phenyl-propyl}-carbamic acid isopropyl ester hydrochloride | 593.95 | 97+ (HPLC) |
| 85 | 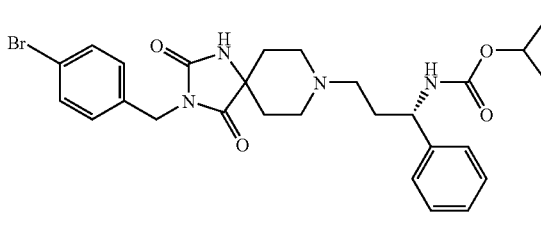 HCl | {(S)-3-[3-(4-Bromo-benzyl)-2,4-dioxo-1,3,8-triaza-spiro[4.5]dec-8-yl]-1-phenyl-propyl}-carbamic acid cyclopentyl ester hydrochloride | 619.99 | 98+ (HPLC) |
| 86 | 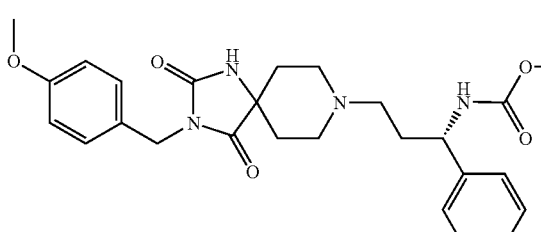 HCl | {(S)-3-[3-(4-Methoxy-benzyl)-2,4-dioxo-1,3,8-triaza-spiro[4.5]dec-8-yl]-1-phenyl-propyl}-carbamic acid methyl ester hydrochloride | 517.03 | 98+ (HPLC) |

TABLE 4-continued

| CPD | STRUCTURE | COMPOUND NAME | MOLWT | PURITY |
|---|---|---|---|---|
| 87 | HCl | {(S)-3-[3-(4-Methoxy-benzyl)-2,4-dioxo-1,3,8-triaza-spiro[4.5]dec-8-yl]-1-phenyl-propyl}-carbamic acid ethyl ester hydrochloride | 531.06 | 97+ (HPLC) |
| 88 | HCl | {(S)-3-[3-(4-Methoxy-benzyl)-2,4-dioxo-1,3,8-triaza-spiro[4.5]dec-8-yl]-1-phenyl-propyl}-carbamic acid isopropyl ester hydrochloride | 545.08 | 99+ (HPLC) |
| 89 | HCl | {(S)-3-[3-(4-Methoxy-benzyl)-2,4-dioxo-1,3,8-triaza-spiro[4.5]dec-8-yl]-1-phenyl-propyl}-carbamic acid cyclopentyl ester hydrochloride | 571.12 | 98+ (HPLC) |
| 90 | HCl | {(S)-3-[3-(4-Methanesulfonyl-benzyl)-2,4-dioxo-1,3,8-triaza-spiro[4.5]dec-8-yl]-1-phenyl-propyl}-carbamic acid methyl ester hydrochloride | 565.09 | 98+ (HPLC) |
| 91 | HCl | {(S)-3-[3-(4-Methanesulfonyl-benzyl)-2,4-dioxo-1,3,8-triaza-spiro[4.5]dec-8-yl]-1-phenyl-propyl}-carbamic acid ethyl ester hydrochloride | 579.12 | 97+ (HPLC) |

TABLE 4-continued

| CPD | STRUCTURE | COMPOUND NAME | MOLWT | PURITY |
|---|---|---|---|---|
| 92 | HCl | {(S)-3-[3-(4-Methanesulfonyl-benzyl)-2,4-dioxo-1,3,8-triaza-spiro[4.5]dec-8-yl]-1-phenyl-propyl}-carbamic acid isopropyl ester hydrochloride | 593.15 | 99+ (HPLC) |
| 93 | HCl | {(S)-3-[3-(4-Methanesulfonyl-benzyl)-2,4-dioxo-1,3,8-triaza-spiro[4.5]dec-8-yl]-1-phenyl-propyl}-carbamic acid cyclopentyl ester hydrochloride | 619.18 | 98+ (HPLC) |

Scheme 5

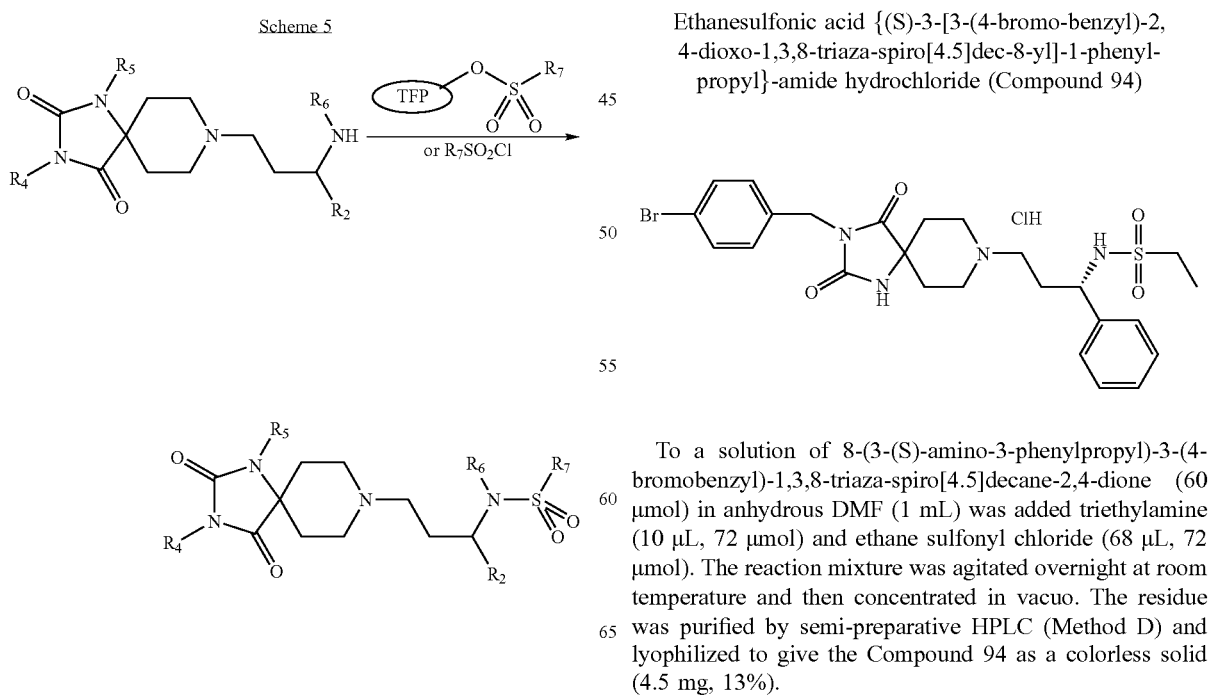

Example 7

Ethanesulfonic acid {(S)-3-[3-(4-bromo-benzyl)-2,4-dioxo-1,3,8-triaza-spiro[4.5]dec-8-yl]-1-phenyl-propyl}-amide hydrochloride (Compound 94)

To a solution of 8-(3-(S)-amino-3-phenylpropyl)-3-(4-bromobenzyl)-1,3,8-triaza-spiro[4.5]decane-2,4-dione (60 µmol) in anhydrous DMF (1 mL) was added triethylamine (10 µL, 72 µmol) and ethane sulfonyl chloride (68 µL, 72 µmol). The reaction mixture was agitated overnight at room temperature and then concentrated in vacuo. The residue was purified by semi-preparative HPLC (Method D) and lyophilized to give the Compound 94 as a colorless solid (4.5 mg, 13%).

¹H NMR (400 MHz, DMSO-d₆): δ [ppm] 10.46 (br d, 1H), 8.87 (br d, 1H), 7.92 (d, 1H), 7.46 (d, 2H), 7.38-7.22 (m, 5H), 7.13 (d, 2H), 4.44 (s, 2H), 4.34-4.29 (m, 1H), 3.51-3.42 (m, 2H), 3.15-2.90 (m, 4H), 2.72-2.60 (m, 1H), 2.20-1.65 (m, 7H), 0.88 (t, 3H).

Table 5 of compounds illustrates some of the compounds of the present invention which were synthesized using the procedures described in scheme 5.

TABLE 5

| CPD | STRUCTURE | COMPOUND NAME | MOLWT | PURITY |
|---|---|---|---|---|
| 94 | 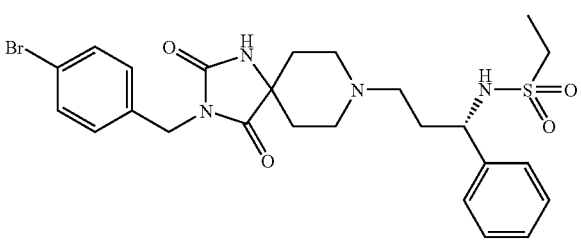 HCl | Ethanesulfonic acid {(S)-3-[3-(4-bromo-benzyl)-2,4-dioxo-1,3,8-triaza-spiro[4.5]dec-8-yl]-1-phenyl-propyl}-amide hydrochloride | 599.98 | 99+ (HPLC) |
| 95 | 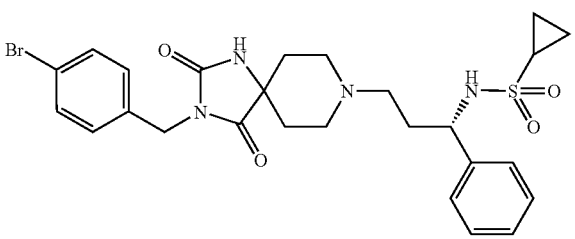 HCl | Cyclopropanesulfonic acid {(S)-3-[3-(4-bromo-benzyl)-2,4-dioxo-1,3,8-triaza-spiro[4.5]dec-8-yl]-1-phenyl-propyl}-amide hydrochloride | 611.99 | 98+ (HPLC) |
| 96 | 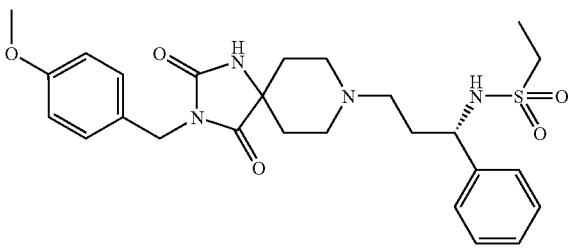 HCl | Ethanesulfonic acid {(S)-3-[3-(4-methoxy-benzyl)-2,4-dioxo-1,3,8-triaza-spiro[4.5]dec-8-yl]-1-phenyl-propyl}-amide hydrochloride | 551.11 | 98+ (HPLC) |
| 97 | 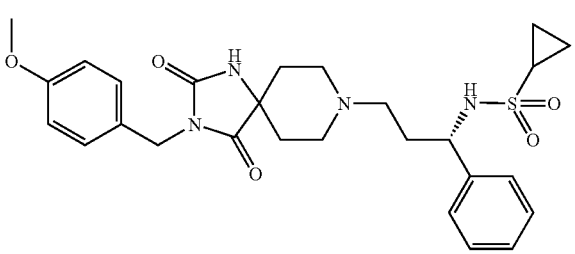 HCl | Cyclopropanesulfonic acid {(S)-3-[3-(4-methoxy-benzyl)-2,4-dioxo-1,3,8-triaza-spiro[4.5]dec-8-yl]-1-phenyl-propyl}-amide hydrochloride | 563.12 | 98+ (HPLC) |

TABLE 5-continued

| CPD | STRUCTURE | COMPOUND NAME | MOLWT | PURITY |
|---|---|---|---|---|
| 98 | HCl | Ethanesulfonic acid {(S)-3-[3-(4-methanesulfonyl-benzyl)-2,4-dioxo-1,3,8-triaza-spiro[4.5]dec-8-yl]-1-phenyl propyl}-amide hydrochloride | 599.17 | 98+ (HPLC) |
| 99 | HCl | Cyclopropanesulfonic acid {(S)-3-[3-(4-methanesulfonyl-benzyl)-2,4-dioxo-1,3,8-triaza-spiro[4.5]dec-8-yl]-1-phenyl-propyl}-amide hydrochloride | 611.18 | 99+ (HPLC) |

Table 6 of compounds illustrates some additional compounds of the present invention which can be synthesized using the procedures described in scheme 2.

TABLE 6

| CPD | STRUCTURE | COMPOUND NAME | MOLWT |
|---|---|---|---|
| 100 | HCl | N-{(S)-3-[3-(4-Bromo-benzyl)-1-methyl-2,4-dioxo-1,3,8-triaza-spiro[4.5]dec-8-yl]-1-phenyl-propyl}-isobutyramide hydrochloride | 591.98 |
| 101 | HCl | N-{(S)-3-[3-(4-Bromo-benzyl)-1-ethyl-2,4-dioxo-1,3,8-triaza-spiro[4.5]dec-8-yl]-1-phenyl-propyl}-isobutyramide hydrochloride | 606.01 |

TABLE 6-continued

| CPD | STRUCTURE | COMPOUND NAME | MOLWT |
|---|---|---|---|
| 102 | 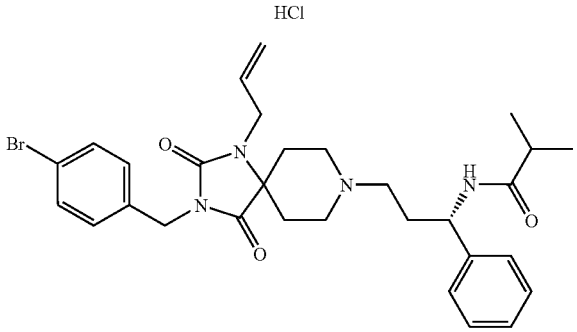 HCl | N-{(S)-3-[1-Allyl-3-(4-bromo-benzyl)-2,4-dioxo-1,3,8-triaza-spiro[4.5]dec-8-yl]-1-phenyl-propyl}-isobutyramide hydrochloride | 618.02 |
| 103 | 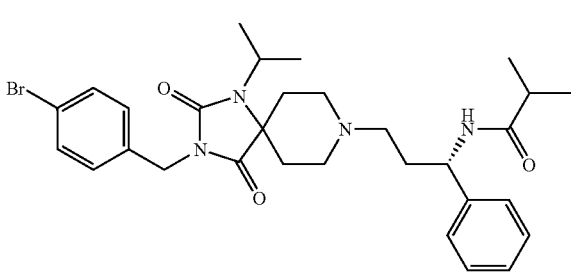 HCl | N-{(S)-3-[3-(4-Bromo-benzyl)-1-isopropyl-2,4-dioxo-1,3,8-triaza-spiro[4.5]dec-8-yl]-1-phenyl-propyl}-isobutyramide hydrochloride | 620.03 |
| 104 | 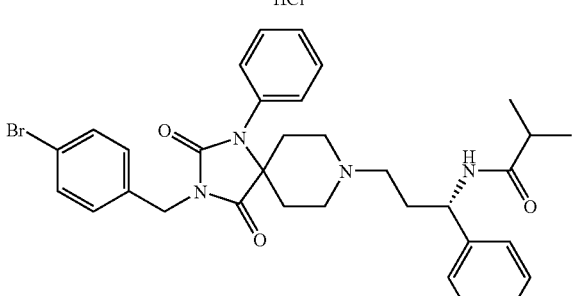 HCl | N-{(S)-3-[3-(4-Bromo-benzyl)-2,4-dioxo-1-phenyl-1,3,8-triaza-spiro[4.5]dec-8-yl]-1-phenyl-propyl}-isobutyramide hydrochloride | 654.05 |
| 105 | 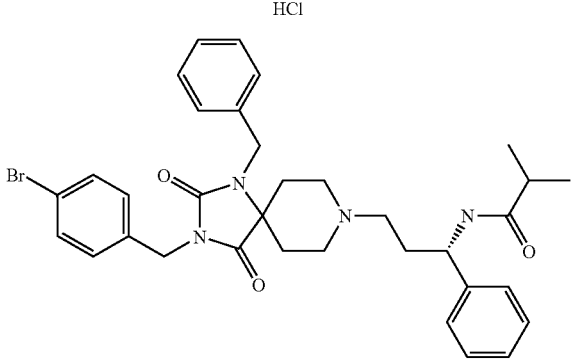 HCl | N-{(S)-3-[1-Benzyl-3-(4-bromo-benzyl)-2,4-dioxo-1,3,8-triaza-spiro[4.5]dec-8-yl]-1-phenyl-propyl}-isobutyramide hydrochloride | 668.08 |

TABLE 6-continued

| CPD | STRUCTURE | COMPOUND NAME | MOLWT |
|---|---|---|---|
| 106 | 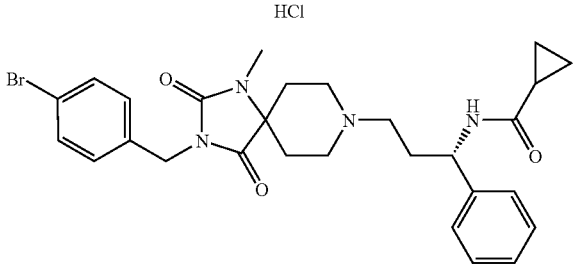 HCl | Cyclopropanecarboxylic acid {(S)-3-[3-(4-bromo-benzyl)-1-methyl-2,4-dioxo-1,3,8-triaza-spiro[4.5]dec-8-yl]-1-phenyl-propyl}-amide hydrochloride | 589.96 |
| 107 | 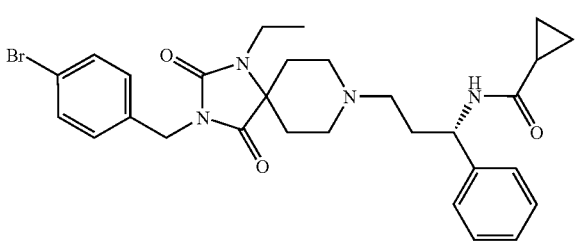 HCl | Cyclopropanecarboxylic acid {(S)-3-[3-(4-bromo-benzyl)-1-ethyl-2,4-dioxo-1,3,8-triaza-spiro[4.5]dec-8-yl]-1-phenyl-propyl}-amide hydrochloride | 603.99 |
| 108 | 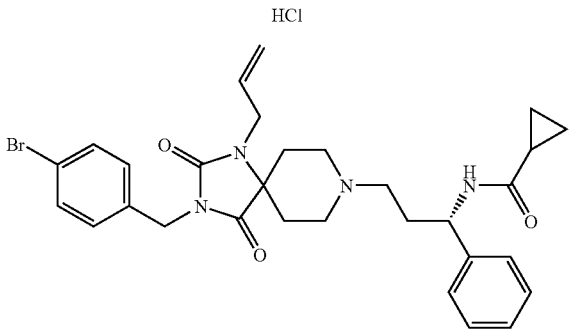 HCl | Cyclopropanecarboxylic acid {(S)-3-[1-allyl-3-(4-bromo-benzyl)-2,4-dioxo-1,3,8-triaza-spiro[4.5]dec-8-yl]-1-phenyl-propyl}-amide hydrochloride | 616 |
| 109 | 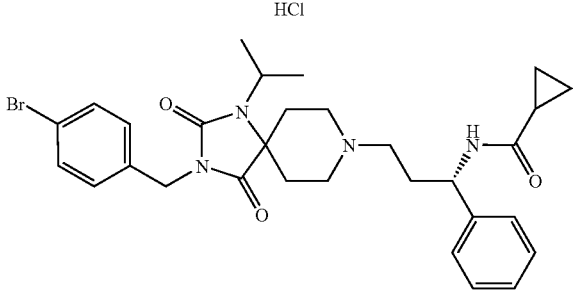 HCl | Cyclopropanecarboxylic acid {(S)-3-[3-(4-bromo-benzyl)-1-isopropyl-2,4-dioxo-1,3,8-triaza-spiro[4.5]dec-8-yl]-1-phenyl-propyl}-amide hydrochloride | 618.02 |
| 110 | 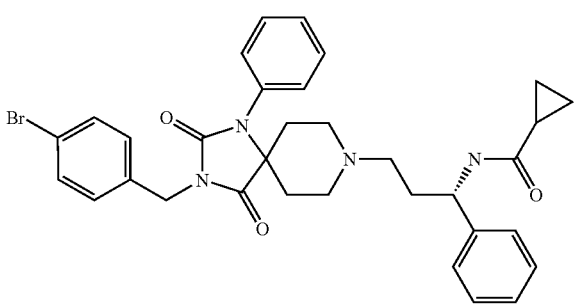 HCl | Cyclopropanecarboxylic acid {(S)-3-[3-(4-bromo-benzyl)-2,4-dioxo-1-phenyl-1,3,8-triaza-spiro[4.5]dec-8-yl]-1-phenyl-propyl}-amide hydrochloride | 652.04 |

TABLE 6-continued

| CPD | STRUCTURE | COMPOUND NAME | MOLWT |
|-----|-----------|---------------|-------|
| 111 | HCl | Cyclopropanecarboxylic acid {(S)-3-[1-benzyl-3-(4-bromo-benzyl)-2,4-dioxo-1,3,8-triaza-spiro[4.5]dec-8-yl]-1-phenyl-propyl}-amide hydrochloride | 666.06 |
| 112 | HCl | 4,4-Difluoro-cyclohexanecarboxylic acid {(S)-3-[3-(4-bromo-benzyl)-1-methyl-2,4-dioxo-1,3,8-triaza-spiro[4.5]dec-8-yl]-1-phenyl-propyl}-amide hydrochloride | 668.03 |
| 113 | HCl | 4,4-Difluoro-cyclohexanecarboxylic acid {(S)-3-[3-(4-bromo-benzyl)-1-ethyl-2,4-dioxo-1,3,8-triaza-spiro[4.5]dec-8-yl]-1-phenyl-propyl}-amide hydrochloride | 682.05 |
| 114 | HCl | 4,4-Difluoro-cyclohexanecarboxylic acid {(S)-3-[1-allyl-3-(4-bromo-benzyl)-2,4-dioxo-1,3,8-triaza-spiro[4.5]dec-8-yl]-1-phenyl-propyl}-amide hydrochloride | 694.06 |

TABLE 6-continued

| CPD | STRUCTURE | COMPOUND NAME | MOLWT |
|---|---|---|---|
| 115 | HCl | 4,4-Difluoro-cyclohexanecarboxylic acid {(S)-3-[3-(4-bromo-benzyl)-1-isopropyl-2,4-dioxo-1,3,8-triaza-spiro[4.5]dec-8-yl]-1-phenyl-propyl}-amide hydrochloride | 696.08 |
| 116 | HCl | 4,4-Difluoro-cyclohexanecarboxylic acid {(S)-3-[3-(4-bromo-benzyl)-2,4-dioxo-1-phenyl-1,3,8-triaza-spiro[4.5]dec-8-yl]-1-phenyl-propyl}-amide hydrochloride | 730.13 |
| 117 | HCl | 4-Difluoro-cyclohexanecarboxylic acid {(S)-3-[1-benzyl-3-(4-bromo-benzyl)-2,4-dioxo-1,3,8-triaza-spiro[4.5]dec-8-yl]-1-phenyl-propyl}-amide hydrochloride | 744.13 |

Example 8

The following assay methods are suitable for evaluating the compounds of the invention.

Chemokine Binding assay: Membranes (1 μg/well) from human embryonic kidney (HEK-293) cells expressing human CCR5 were incubated with 0.1 nM $^{125}$I-labeled MIP-1α (Amersham) in the presence of varying concentrations of a test compound (10000-0.01 nM) in buffer (50 mM Hepes, pH 7.3/5 mM MgCl$_2$/1 mM CaCl$_2$/0.5% BSA) for 90 min at room temperature. Reaction mixtures (100 μL) were filtered through Multiscreen GFB filters (Millipore) and washed six times with cold wash buffer (50 mM Hepes, pH 7.3/0.5 M NaCl, 0.1% BSA). Bound $^{125}$I-MIP-1α was quantitated by liquid scintillation counting. The nonspecific binding of $^{125}$I-labeled MIP-1α to the membrane was determined based on the radioactivity from the wells added with 100 nM non-radiolabeled MIP-1α. IC$_{50}$ and K$_D$ values were calculated by using GRAPHPAD PRISM software (Intuitive Software for Science, San Diego).

HIV-1 Replication in PBMC Cultures: Isolated PBMCs were stimulated in vitro with 5 μg/ml phytohemaglutinin and 50 units/ml IL-2 for 3 days. The cells were resuspended at 4×10$^6$/ml in complete medium (RPMI, 10% FBS/50 units/ml IL-2), seeded into 96-well plates (2×10$^5$/well), incubated with inhibitor for 1 h at 37° C., and infected in triplicate with 25-100 tissue culture 50% infective dose (TCID$_{50}$) per well of the R5 HIV-1$_{JR-FL}$ strain for 3-4 h. The cells were washed twice in PBS to remove residual virus and cultured in the presence of inhibitor for 4-6 days. HIV-1 replication was determined by the presence of viral RT activity in harvested supernatant fluid. The IC$_{50}$ values for the virus were determined by using GRAPHPAD PRISM software.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound according to formula (I):

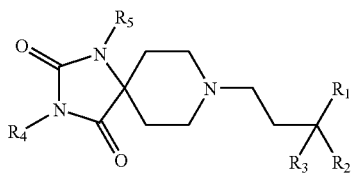
(I)

or a pharmaceutically acceptable salt thereof, wherein
$R_1$ is

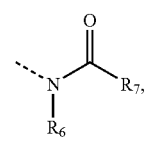
(II)

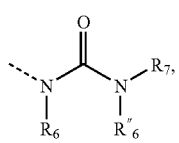
(III)

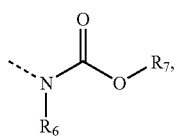
(IV)

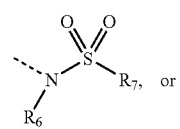
(V)

or

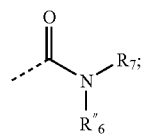
(VI)

$R_2$ is optionally substituted $C_{1-10}$ alkyl, optionally substituted $C_{2-10}$ alkenyl, optionally substituted $C_{2-10}$ alkynyl, optionally substituted $C_{6-12}$ aryl or optionally substituted 3 to 10 membered heterocycle;

$R_3$ is H, optionally substituted $C_{1-10}$ alkyl, optionally substituted $C_{2-10}$ alkenyl, optionally substituted $C_{2-10}$ alkynyl, or optionally substituted $C_{6-12}$ aryl;

$R_4$ and $R_5$ are each independently H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{6-12}$ aralkyl or optionally substituted 3 to 10 membered heteroaralkyl;

$R_6$ and $R''_6$ are each independently H, optionally substituted $C_{1-10}$ alkyl, optionally substituted $C_{2-10}$ alkenyl, or optionally substituted $C_{2-10}$ alkynyl, and $R_7$ is H, optionally substituted $C_{10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{6-12}$ aralkyl or optionally substituted 3 to 10 membered heteroaralkyl, or $R''_6$ and $R_7$ can be taken together to form an optionally substituted 3 to 10 membered heterocycle.

2. A compound according to claim 1, wherein $R_1$ is

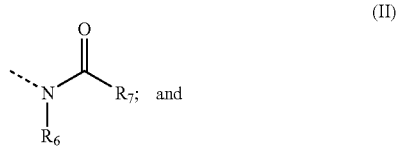
(II)

$R_7$ is optionally substituted $C_{1-10}$ alkyl, $C_{6-12}$ aryl or optionally substituted 3 to 10 membered heterocycle.

3. A compound according to claim 1, wherein $R_7$ is methyl, ethyl, isopropyl, cyclopropyl, cyclobutyl, cyclopentyl, cyclohexyl, cycloheptyl, 4,4-difluorocyclohexyl, $CH_2$-cyclopropyl, $CH_2$-cyclobutyl, $CH_2$-cyclopentyl, $CH_2$-cyclohexyl, phenyl, phenyl substituted with at least one methyl, phenyl substituted with at least one halogen, phenyl substituted with at least one Cl, phenyl substituted with Br, phenyl substituted with F, phenyl substituted with at least one methoxy, benzyl, benzyl substituted with at least one methyl, benzyl substituted with at least one halogen, benzyl substituted with at least one Cl, benzyl substituted with at least one Br, benzyl substituted with at least one F, benzyl substituted with at least one methoxy, or pyridinyl.

4. A compound according to claim 1, wherein $R_1$ is:

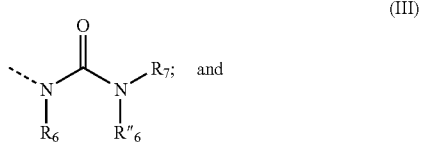
(III)

$R_7$ is optionally substituted $C_{6-12}$ aryl, or $R''_6$ and $R_7$ together form an optionally substituted 3 to 10 membered heterocycle.

5. A compound according to claim 4, wherein $R_7$ is phenyl, phenyl substituted with at least one methyl, phenyl substituted with halogen, phenyl substituted with at least one halogen, phenyl substituted with at least one Br, phenyl substituted with at least one F, phenyl substituted with at least one Cl, phenyl substituted with methoxy, or naphthyl.

6. A compound according to claim 4, wherein $R''_6$ and $R_7$ together form an optionally substituted piperidine, a substituted morpholine, morpholine, an optionally substituted pyrrolidine, or 3,3-difluoropyrrolidine.

7. A compound according to claim 1, wherein $R_1$ is:

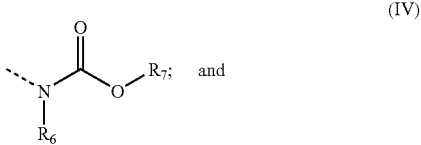
(IV)

$R_7$ is optionally substituted $C_{1-10}$ alkyl.

8. A compound according to claim 7, wherein R_7 is methyl, ethyl, tert-butyl, cyclobutyl, cyclopentyl, or cyclohexyl.

9. A compound according to claim 1, wherein R_1 is:

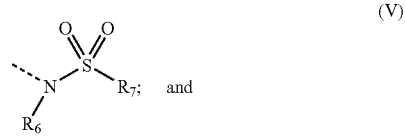

(V)

R_7 is optionally substituted $C_{1-10}$ alkyl, optionally substituted $C_{6-12}$ aryl or optionally substituted 3 to 10 membered heterocycle.

10. A compound according to claim 9, wherein R_7 is optionally substituted phenyl, or optionally substituted $C_{1-10}$ alkyl.

11. A compound according to claim 1, wherein R_1 is:

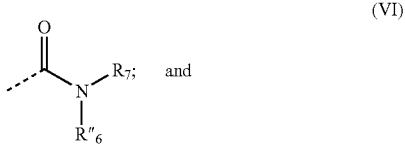

(VI)

R_7 is optionally substituted $C_{1-10}$ alkyl or optionally substituted $C_{6-12}$ aryl.

12. A compound according to claim 11, wherein R_7 is cyclohexyl, or phenyl.

13. A compound according to claim 1, wherein R_2 is optionally substituted $C_{6-12}$ aryl or optionally substituted 3 to 10 membered heterocycle.

14. A compound according to claim 13, wherein R_2 is phenyl, phenyl substituted with at least one halogen, phenyl substituted with at least one Cl, phenyl substituted with at least one F, or phenyl substituted with at least one methoxy.

15. A compound according to claim 13, wherein R_2 is thienyl or pyridyl.

16. A compound according to claim 1, wherein R_3 is H, optionally substituted $C_{1-4}$ alkyl, or methyl.

17. A compound according to claim 1, wherein R_4 is $C_{6-12}$ aralkyl or $C_{6-12}$ heteroaralkyl.

18. A compound according to claim 17, wherein R_4 is optionally substituted $C_{6-12}$ aralkyl.

19. A compound according to claim 17, wherein R_4 is optionally substituted $C_{6-12}$ heteroaralkyl.

20. A compound according to claim 17, wherein R_4 is benzyl, benzyl substituted with halogen, benzyl substituted with Br, benzyl substituted with F, benzyl substituted with Cl, benzyl substituted with a $C_{1-3}$ alkoxy, benzyl substituted with methoxy, benzyl substituted with $SO_2C_{1-3}$alkyl, benzyl substituted with methanesulfonyl, benzyl substituted with difluoromethoxy, benzyl substituted with trifluoromethoxy, benzyl substituted with trifluoromethyl, benzyl substituted with CN, benzyl substituted with pyrrazoyl, benzyl optionally substituted in the para (p) position, or pyridinyl-methyl.

21. A compound according to claim 1, wherein R_5 is H, optionally substituted $C_{1-4}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{6-12}$ aralkyl or optionally substituted 3 to 10 membered heteroaralkyl.

22. A compound according to claim 21, wherein R_5 is optionally substituted $C_{1-4}$ alkyl, methyl, ethyl, or isopropyl.

23. A compound according to claim 21, wherein R_5 is optionally substituted $C_{2-10}$ alkenyl, optionally substituted $C_{2-10}$ alkynyl, or allyl.

24. A compound according to claim 21, wherein R_5 is optionally substituted $C_{6-12}$ aryl, optionally substituted 3 to 10 membered heterocycle, or phenyl.

25. A compound according to claim 21, wherein R_5 is optionally substituted $C_{6-12}$ aralkyl, optionally substituted 3 to 10 membered heteroaralkyl, or benzyl.

26. A compound according to claim 1, wherein said compound is:
- {3-[3-(4-Bromo-benzyl)-2,4-dioxo-1,3,8-triaza-spiro[4.5]dec-8-yl]-1-(S)-phenyl-propyl}-carbamic acid tert-butyl ester,
- (S)-3-(4-Bromobenzyl)-8-(3-isobutyrylamino-3-phenyl-propyl)-2,4-dioxo-1,3,8-triaza-spiro[4.5]decane,
- (S)-3-(4-Bromobenzyl)-8-[3-(cyclopentanecarbonyl-amino)-3-phenyl-propyl]-2,4-dioxo-1,3,8-triaza-spiro[4.5]decane,
- (S)-3-(4-Bromobenzyl)-8-[3-(cyclohexanecarbonyl-amino)-3-phenyl-propyl]-2,4-dioxo-1,3,8-triaza-spiro[4.5]decane,
- Cyclopentanecarboxylic acid {3-(S)-[3-(4-methoxy-benzyl)-2,4-dioxo-1,3,8-triaza-spiro[4.5]dec-8-yl]-1-phenyl-propyl}-amide,
- Cyclopropanecarboxylic acid {3-(S)-[3-(4-methoxy-benzyl)-2,4-dioxo-1,3,8-triaza-spiro[4.5]dec-8-yl]-1-phenyl-propyl}-amide,
- N-{(S)-3-[3-(4-Bromo-benzyl)-2,4-dioxo-1,3,8-triaza-spiro[4.5]dec-8-yl]-1-phenyl-propyl}-benzamide,
- N-{(S)-3-[3-(4-Bromo-benzyl)-2,4-dioxo-1,3,8-triaza-spiro[4.5]dec-8-yl]-1-phenyl-propyl}-2-phenyl-acetamide,
- N-{(S)-3-[3-(4-Bromo-benzyl)-2,4-dioxo-1,3,8-triaza-spiro[4.5]dec-8-yl]-1-phenyl-propyl}-nicotinamide,
- N-{(S)-3-[3-(4-Bromo-benzyl)-2,4-dioxo-1,3,8-triaza-spiro[4.5]dec-8-yl]-1-phenyl-propyl}-acetamide,
- N-{(S)-3-[3-(4-Bromo-benzyl)-2,4-dioxo-1,3,8-triaza-spiro[4.5]dec-8-yl]-1-phenyl-propyl}-propionamide,
- N-{(S)-3-[3-(4-Bromo-benzyl)-2,4-dioxo-1,3,8-triaza-spiro[4.5]dec-8-yl]-1-phenyl-propyl}-2,2-dimethyl-propionamide,
- Cyclopropanecarboxylic acid {(S)-3-[3-(4-bromo-benzyl)-2,4-dioxo-1,3,8-triaza-spiro[4.5]dec-8-yl]-1-phenyl-propyl}-amide,
- 1-Methyl-cyclopropanecarboxylic acid {(S)-3-[3-(4-bromo-benzyl)-2,4-dioxo-1,3,8-triaza-spiro[4.5]dec-8-yl]-1-phenyl-propyl}-amide,
- N-{(S)-3-[3-(4-Bromo-benzyl)-2,4-dioxo-1,3,8-triaza-spiro[4.5]dec-8-yl]-1-phenyl-propyl}-2-cyclopropyl-acetamide,
- Cyclobutanecarboxylic acid {(S)-3-[3-(4-bromo-benzyl)-2,4-dioxo-1,3,8-triaza-spiro[4.5]dec-8-yl]-1-phenyl-propyl}-amide,
- 4,4-Difluoro-cyclohexanecarboxylic acid {(S)-3-[3-(4-bromo-benzyl)-2,4-dioxo-1,3,8-triaza-spiro[4.5]dec-8-yl]-1-phenyl-propyl}-amide,
- Tetrahydro-pyran-4-carboxylic acid {(S)-3-[3-(4-bromo-benzyl)-2,4-dioxo-1,3,8-triaza-spiro[4.5]dec-8-yl]-1-phenyl-propyl}-amide,
- N-{(S)-3-[3-(4-Methoxy-benzyl)-2,4-dioxo-1,3,8-triaza-spiro[4.5]dec-8-yl]-1-phenyl-propyl}-benzamide,
- N-{(S)-3-[3-(4-Methoxy-benzyl)-2,4-dioxo-1,3,8-triaza-spiro[4.5]dec-8-yl]-1-phenyl-propyl}-2-phenyl-acetamide, N-{(S)-3-[3-(4-Methoxy-benzyl)-2,4-dioxo-1,3,8-triaza-spiro[4.5]dec-8-yl]-1-phenyl-propyl}-nicotinamide,
N-{(S)-3-[3-(4-Methoxy-benzyl)-2,4-dioxo-1,3,8-triaza-spiro[4.5]dec-8-yl]-1-phenyl-propyl}-acetamide,
N-{(S)-3-[3-(4-Methoxy-benzyl)-2,4-dioxo-1,3,8-triaza-spiro[4.5]dec-8-yl]-1-phenyl-propyl}-propionamide,
N-{(S)-3-[3-(4-Methoxy-benzyl)-2,4-dioxo-1,3,8-triaza-spiro[4.5]dec-8-yl]-1-phenyl-propyl}-isobutyramide,
N-{(S)-3-[3-(4-Methoxy-benzyl)-2,4-dioxo-1,3,8-triaza-spiro[4.5]dec-8-yl]-1-phenyl-propyl}-2,2-dimethyl-propionamide,
1-Methyl-cyclopropanecarboxylic acid {(S)-3-[3-(4-methoxy-benzyl)-2,4-dioxo-1,3,8-triaza-spiro[4.5]dec-8-yl]-1-phenyl-propyl}-amide,
2-Cyclopropyl-N-{(S)-3-[3-(4-methoxy-benzyl)-2,4-dioxo-1,3,8-triaza-spiro[4.5]dec-8-yl]-1-phenyl-propyl}-acetamide,
Cyclobutanecarboxylic acid {(S)-3-[3-(4-methoxy-benzyl)-2,4-dioxo-1,3,8-triaza-spiro[4.5]dec-8-yl]-1-phenyl-propyl}-amide,
Cyclohexanecarboxylic acid {(S)-3-[3-(4-methoxy-benzyl)-2,4-dioxo-1,3,8-triaza-spiro[4.5]dec-8-yl]-1-phenyl-propyl}-amide,
4,4-Difluoro-cyclohexanecarboxylic acid {(S)-3-[3-(4-methoxy-benzyl)-2,4-dioxo-1,3,8-triaza-spiro[4.5]dec-8-yl]-1-phenyl-propyl}-amide,
Tetrahydro-pyran-4-carboxylic acid {(S)-3-[3-(4-methoxy-benzyl)-2,4-dioxo-1,3,8-triaza-spiro[4.5]dec-8-yl]-1-phenyl-propyl}-amide,
N-{(S)-3-[3-(4-Methanesulfonyl-benzyl)-2,4-dioxo-1,3,8-triaza-spiro[4.5]dec-8-yl]-1-phenyl-propyl}-benzamide,
N-{(S)-3-[3-(4-Methanesulfonyl-benzyl)-2,4-dioxo-1,3,8-triaza-spiro[4.5]dec-8-yl]-1-phenyl-propyl}-2-phenyl-acetamide,
N-{(S)-3-[3-(4-Methanesulfonyl-benzyl)-2,4-dioxo-1,3,8-triaza-spiro[4.5]dec-8-yl]-1-phenyl-propyl}-nicotinamide,
N-{(S)-3-[3-(4-Methanesulfonyl-benzyl)-2,4-dioxo-1,3,8-triaza-spiro[4.5]dec-8-yl]-1-phenyl-propyl}-acetamide,
N-{(S)-3-[3-(4-Methanesulfonyl-benzyl)-2,4-dioxo-1,3,8-triaza-spiro[4.5]dec-8-yl]-1-phenyl-propyl}-propionamide,
N-{(S)-3-[3-(4-Methanesulfonyl-benzyl)-2,4-dioxo-1,3,8-triaza-spiro[4.5]dec-8-yl]-1-phenyl-propyl}-isobutyramide,
N-{(S)-3-[3-(4-Methanesulfonyl-benzyl)-2,4-dioxo-1,3,8-triaza-spiro[4.5]dec-8-yl]-1-phenyl-propyl}-2,2-dimethyl-propionamide,
Cyclopropanecarboxylic acid {(S)-3-[3-(4-methanesulfonyl-benzyl)-2,4-dioxo-1,3,8-triaza-spiro[4.5]dec-8-yl]-1-phenyl-propyl}-amide,
1-Methyl-cyclopropanecarboxylic acid {(S)-3-[3-(4-methanesulfonyl-benzyl)-2,4-dioxo-1,3,8-triaza-spiro[4.5]dec-8-yl]-1-phenyl-propyl}-amide,
2-Cyclopropyl-N-{(S)-3-[3-(4-methanesulfonyl-benzyl)-2,4-dioxo-1,3,8-triaza-spiro[4.5]dec-8-yl]-1-phenyl-propyl}-acetamide,
Cyclobutanecarboxylic acid {(S)-3-[3-(4-methanesulfonyl-benzyl)-2,4-dioxo-1,3,8-triaza-spiro[4.5]dec-8-yl]-1-phenyl-propyl}-amide,
Cyclopentanecarboxylic acid {(S)-3-[3-(4-methanesulfonyl-benzyl)-2,4-dioxo-1,3,8-triaza-spiro[4.5]dec-8-yl]-1-phenyl-propyl}-amide,
Cyclohexanecarboxylic acid {(S)-3-[3-(4-methanesulfonyl-benzyl)-2,4-dioxo-1,3,8-triaza-spiro[4.5]dec-8-yl]-1-phenyl-propyl}-amide,
4,4-Difluoro-cyclohexanecarboxylic acid {(S)-3-[3-(4-methanesulfonyl-benzyl)-2,4-dioxo-1,3,8-triaza-spiro[4.5]dec-8-yl]-1-phenyl-propyl}-amide,
Tetrahydro-pyran-4-carboxylic acid {(S)-3-[3-(4-methanesulfonyl-benzyl)-2,4-dioxo-1,3,8-triaza-spiro[4.5]dec-8-yl]-1-phenyl-propyl}-amide,
N-{(S)-3-[3-(4-Methoxy-benzyl)-1-methyl-2,4-dioxo-1,3,8-triaza-spiro[4.5]dec-8-yl]1-phenyl-propyl}-isobutyramide,
Cyclopropanecarboxylic acid {(S)-3-[3-(4-methoxy-benzyl)-1-methyl-2,4-dioxo-1,3,8-triaza-spiro[4.5]dec-8-yl]-1-phenyl-propyl}-amide,
4,4-Difluoro-cyclohexanecarboxylic acid {(S)-3-[3-(4-methoxy-benzyl)-1-methyl-2,4-dioxo-1,3,8-triaza-spiro[4.5]dec-8-yl]-1-phenyl-propyl}-amide,
N-{(S)-3-[3-(4-Fluoro-benzyl)-2,4-dioxo-1,3,8-triaza-spiro[4.5]dec-8-yl]-1-phenyl-propyl}-isobutyramide,
N-{(S)-3-[3-(4-Chloro-benzyl)-2,4-dioxo-1,3,8-triaza-spiro[4.5]dec-8-yl]-1-phenyl-propyl}-isobutyramide,
N-{(S)-3-[3-(4-Cyano-benzyl)-2,4-dioxo-1,3,8-triaza-spiro[4.5]dec-8-yl]-1-phenyl-propyl}-isobutyramide,
N-{(S)-3-[2,4-Dioxo-3-(4-trifluoromethyl-benzyl)-1,3,8-triaza-spiro[4.5]dec-8-yl]-1-phenyl-propyl}-isobutyramide,
N-{(S)-3-[2,4-Dioxo-3-(4-trifluoromethoxy-benzyl)-1,3,8-triaza-spiro[4.5]dec-8-yl]-1-phenyl-propyl}-isobutyramide,
N-{(S)-3-[2,4-Dioxo-3-(4-pyrazol-1-yl-benzyl)-1,3,8-triaza-spiro[4.5]dec-8-yl]-1-phenyl-propyl}-isobutyramide,
Cyclopropanecarboxylic acid {(S)-3-[3-(4-fluoro-benzyl)-2,4-dioxo-1,3,8-triaza-spiro[4.5]dec-8-yl]-1-phenyl-propyl}-amide,
Cyclopropanecarboxylic acid {(S)-3-[3-(4-chloro-benzyl)-2,4-dioxo-1,3,8-triaza-spiro[4.5]dec-8-yl]-1-phenyl-propyl}-amide,
Cyclopropanecarboxylic acid {(S)-3-[3-(4-cyano-benzyl)-2,4-dioxo-1,3,8-triaza-spiro[4.5]dec-8-yl]-1-phenyl-propyl}-amide,
Cyclopropanecarboxylic acid {(S)-3-[3-(4-difluoromethoxy-benzyl)-2,4-dioxo-1,3,8-triaza-spiro[4.5]dec-8-yl]-1-phenyl-propyl}-amide,
Cyclopropanecarboxylic acid {(S)-3-[2,4-dioxo-3-(4-trifluoromethyl-benzyl)-1,3,8-triaza-spiro[4.5]dec-8-yl]-1-phenyl-propyl}-amide,
Cyclopropanecarboxylic acid {(S)-3-[2,4-dioxo-3-(4-trifluoromethoxy-benzyl)-1,3,8-triaza-spiro[4.5]dec-8-yl]-1-phenyl-propyl}-amide,
Cyclopropanecarboxylic acid {(S)-3-[2,4-dioxo-3-(4-pyrazol-1-yl-benzyl)-1,3,8-triaza-spiro[4.5]dec-8-yl]-1-phenyl-propyl}-amide,
Morpholine-4-carboxylic acid {(S)-3-[3-(4-bromo-benzyl)-2,4-dioxo-1,3,8-triaza-spiro[4.5]dec-8-yl]-1-phenyl-propyl}-amide,
Pyrrolidine-1-carboxylic acid {(S)-3-[3-(4-bromo-benzyl)-2,4-dioxo-1,3,8-triaza-spiro[4.5]dec-8-yl]-1-phenyl-propyl}-amide,
3,3-Difluoro-pyrrolidine-1-carboxylic acid {(S)-3-[3-(4-bromo-benzyl)-2,4-dioxo-1,3,8-triaza-spiro[4.5]dec-8-yl]-1-phenyl-propyl}-amide,
3-{(S)-3-[3-(4-Bromo-benzyl)-2,4-dioxo-1,3,8-triaza-spiro[4.5]dec-8-yl]-1-phenyl-propyl}-1,1-dimethyl-urea, 1-{(S)-3-[3-(4-Bromo-benzyl)-2,4-dioxo-1,3,8-triaza-spiro[4.5]dec-8-yl]-1-phenyl-propyl}-3-cyclopentyl-urea,
Morpholine-4-carboxylic acid {(S)-3-[3-(4-methoxy-benzyl)-2,4-dioxo-1,3,8-triaza-spiro[4.5]dec-8-yl]-1-phenyl-propyl}-amide,
Pyrrolidine-1-carboxylic acid {(S)-3-[3-(4-methoxy-benzyl)-2,4-dioxo-1,3,8-triaza-spiro[4.5]dec-8-yl]-1-phenyl-propyl}-amide,
3,3-Difluoro-pyrrolidine-1-carboxylic acid {(S)-3-[3-(4-methoxy-benzyl)-2,4-dioxo-1,3,8-triaza-spiro[4.5]dec-8-yl]-1-phenyl-propyl}-amide,
3-{(S)-3-[3-(4-Methoxy-benzyl)-2,4-dioxo-1,3,8-triaza-spiro[4.5]dec-8-yl]-1-phenyl-propyl}-1,1-dimethyl-urea,
1-Cyclopentyl-3-{(S)-3-[3-(4-methoxy-benzyl)-2,4-dioxo-1,3,8-triaza-spiro[4.5]dec-8-yl]-1-phenyl-propyl}-urea,
Morpholine-4-carboxylic acid {(S)-3-[3-(4-methanesulfonyl-benzyl)-2,4-dioxo-1,3,8-triaza-spiro[4.5]dec-8-yl]-1-phenyl-propyl}-amide,
Pyrrolidine-1-carboxylic acid {(S)-3-[3-(4-methanesulfonyl-benzyl)-2,4-dioxo-1,3,8-triaza-spiro[4.5]dec-8-yl]-1-phenyl-propyl}-amide,
3,3-Difluoro-pyrrolidine-1-carboxylic acid {(S)-3-[3-(4-methanesulfonyl-benzyl)-2,4-dioxo-1,3,8-triaza-spiro[4.5]dec-8-yl]-1-phenyl-propyl}-amide,
3-{(S)-3-[3-(4-Methanesulfonyl-benzyl)-2,4-dioxo-1,3,8-triaza-spiro[4.5]dec-8-yl]-1-phenyl-propyl}-1,1-dimethyl-urea,
1-Cyclopentyl-3-{(S)-3-[3-(4-methanesulfonyl-benzyl)-2,4-dioxo-1,3,8-triaza-spiro[4.5]dec-8-yl]-1-phenyl-propyl}-urea,
{(S)-3-[3-(4-Bromo-benzyl)-2,4-dioxo-1,3,8-triaza-spiro[4.5]dec-8-yl]-1-phenyl-propyl}-carbamic acid methyl ester,
{(S)-3-[3-(4-Bromo-benzyl)-2,4-dioxo-1,3,8-triaza-spiro[4.5]dec-8-yl]-1-phenyl-propyl}-carbamic acid ethyl ester,
{(S)-3-[3-(4-Bromo-benzyl)-2,4-dioxo-1,3,8-triaza-spiro[4.5]dec-8-yl]-1-phenyl-propyl}-carbamic acid isopropyl ester,
{(S)-3-[3-(4-Bromo-benzyl)-2,4-dioxo-1,3,8-triaza-spiro[4.5]dec-8-yl]-1-phenyl-propyl}-carbamic acid cyclopentyl ester,
{(S)-3-[3-(4-Methoxy-benzyl)-2,4-dioxo-1,3,8-triaza-spiro[4.5]dec-8-yl]-1-phenyl-propyl}-carbamic acid methyl ester,
{(S)-3-[3-(4-Methoxy-benzyl)-2,4-dioxo-1,3,8-triaza-spiro[4.5]dec-8-yl]-1-phenyl-propyl}-carbamic acid ethyl ester,
{(S)-3-[3-(4-Methoxy-benzyl)-2,4-dioxo-1,3,8-triaza-spiro[4.5]dec-8-yl]-1-phenyl-propyl}-carbamic acid isopropyl ester,
{(S)-3-[3-(4-Methoxy-benzyl)-2,4-dioxo-1,3,8-triaza-spiro[4.5]dec-8-yl]-1-phenyl-propyl}-carbamic acid cyclopentyl ester,
{(S)-3-[3-(4-Methanesulfonyl-benzyl)-2,4-dioxo-1,3,8-triaza-spiro[4.5]dec-8-yl]-1-phenyl-propyl}-carbamic acid methyl ester,
{(S)-3-[3-(4-Methanesulfonyl-benzyl)-2,4-dioxo-1,3,8-triaza-spiro[4.5]dec-8-yl]-1-phenyl-propyl}-carbamic acid ethyl ester,
{(S)-3-[3-(4-Methanesulfonyl-benzyl)-2,4-dioxo-1,3,8-triaza-spiro[4.5]dec-8-yl]-1-phenyl-propyl}-carbamic acid isopropyl ester,
{(S)-3-[3-(4-Methanesulfonyl-benzyl)-2,4-dioxo-1,3,8-triaza-spiro[4.5]dec-8-yl]-1-phenyl-propyl}-carbamic acid cyclopentyl ester,
Ethanesulfonic acid {(S)-3-[3-(4-bromo-benzyl)-2,4-dioxo-1,3,8-triaza-spiro[4.5]dec-8-yl]-1-phenyl-propyl}-amide,
Cyclopropanesulfonic acid {(S)-3-[3-(4-bromo-benzyl)-2,4-dioxo-1,3,8-triaza-spiro[4.5]dec-8-yl]-1-phenyl-propyl}-amide,
Ethanesulfonic acid {(S)-3-[3-(4-methoxy-benzyl)-2,4-dioxo-1,3,8-triaza-spiro[4.5]dec-8-yl]-1-phenyl-propyl}-amide,
Cyclopropanesulfonic acid {(S)-3-[3-(4-methoxy-benzyl)-2,4-dioxo-1,3,8-triaza-spiro[4.5]dec-8-yl]-1-phenyl-propyl}-amide,
Ethanesulfonic acid {(S)-3-[3-(4-methanesulfonyl-benzyl)-2,4-dioxo-1,3,8-triaza-spiro[4.5]dec-8-yl]-1-phenyl-propyl}-amide,
Cyclopropanesulfonic acid {(S)-3-[3-(4-methanesulfonyl-benzyl)-2,4-dioxo-1,3,8-triaza-spiro[4.5]dec-8-yl]-1-phenyl-propyl}-amide,
N-{(S)-3-[3-(4-Bromo-benzyl)-1-methyl-2,4-dioxo-1,3,8-triaza-spiro[4.5]dec-8-yl]-1-phenyl-propyl}-isobutyramide,
N-{(S)-3-[3-(4-Bromo-benzyl)-1-ethyl-2,4-dioxo-1,3,8-triaza-spiro[4.5]dec-8-yl]-1-phenyl-propyl}-isobutyramide,
N-{(S)-3-[1-Allyl-3-(4-bromo-benzyl)-2,4-dioxo-1,3,8-triaza-spiro[4.5]dec-8-yl]-1-phenyl-propyl}-isobutyramide,
N-{(S)-3-[3-(4-Bromo-benzyl)-1-isopropyl-2,4-dioxo-1,3,8-triaza-spiro[4.5]dec-8-yl]-1-phenyl-propyl}-isobutyramide,
N-{(S)-3-[3-(4-Bromo-benzyl)-2,4-dioxo-1-phenyl-1,3,8-triaza-spiro[4.5]dec-8-yl]-1-phenyl-propyl}-isobutyramide,
N-{(S)-3-[1-Benzyl-3-(4-bromo-benzyl)-2,4-dioxo-1,3,8-triaza-spiro[4.5]dec-8-yl]-1-phenyl-propyl}-isobutyramide,
Cyclopropanecarboxylic acid {(S)-3-(3-(4-bromo-benzyl)-1-methyl-2,4-dioxo-1,3,8-triaza-spiro[4.5]dec-8-yl]-1-phenyl-propyl}-amide,
Cyclopropanecarboxylic acid {(S)-3-[3-(4-bromo-benzyl)-1-ethyl-2,4-dioxo-1,3,8-triaza-spiro[4.5]dec-8-yl]-1-phenyl-propyl}-amide,
Cyclopropanecarboxylic acid {(S)-3-[1-allyl-3-(4-bromo-benzyl)-2,4-dioxo-1,3,8-triaza-spiro[4.5]dec-8-yl]-1-phenyl-propyl}-amide,
Cyclopropanecarboxylic acid {(S)-3-[3-(4-bromo-benzyl)-1-isopropyl-2,4-dioxo-1,3,8-triaza-spiro[4.5]dec-8-yl]-1-phenyl-propyl}-amide,
Cyclopropanecarboxylic acid {(S)-3-[3-(4-bromo-benzyl)-2,4-dioxo-1-phenyl-1,3,8-triaza-spiro[4.5]dec-8-yl]-1-phenyl-propyl}-amide,
Cyclopropanecarboxylic acid {(S)-3-[1-benzyl-3-(4-bromo-benzyl)-2,4-dioxo-1,3,8-triaza-spiro[4.5]dec-8-yl]-1-phenyl-propyl}-amide,
4,4-Difluoro-cyclohexanecarboxylic acid {(S)-3-[3-(4-bromo-benzyl)-1-methyl-2,4-dioxo-1,3,8-triaza-spiro[4.5]dec-8-yl]-1-phenyl-propyl}-amide,
4,4-Difluoro-cyclohexanecarboxylic acid {(S)-3-[3-(4-bromo-benzyl)-1-ethyl-2,4-dioxo-1,3,8-triaza-spiro[4.5]dec-8-yl]-1-phenyl-propyl}-amide,
4,4-Difluoro-cyclohexanecarboxylic acid {(S)-3-[1-allyl-3-(4-bromo-benzyl)-2,4-dioxo-1,3,8-triaza-spiro[4.5]dec-8-yl]-1-phenyl-propyl}-amide, 4,4-Difluoro-cyclohexanecarboxylic acid {(S)-3-[3-(4-bromo-benzyl)-1-isopropyl-2,4-dioxo-1,3,8-triaza-spiro[4.5]dec-8-yl]-1-phenyl-propyl}-amide, 4,4-Difluoro-cyclohexanecarboxylic acid {(S)-3-[3-(4-bromo-benzyl)-2,4-dioxo-1-phenyl-1,3,8-triaza-spiro[4.5]dec-8-yl]-1-phenyl-propyl}-amide, 4,4-Difluoro-cyclohexanecarboxylic acid {(S)-3-[1-benzyl-3-(4-bromo-benzyl)-2,4-dioxo-1,3,8-triaza-spiro[4.5]dec-8-yl]-1-phenyl-propyl}-amide, or a pharmaceutically acceptable salt thereof.

27. A compound according to claim 26, wherein said compound is in the form of a pharmaceutically acceptable salt.

28. A compound according to claim 27, wherein said compound is in the form of a hydrochloride salt.

29. A compound according to claim 1, wherein said compound is a (+) enantiomer having an enantiomeric excess of 99%.

30. A compound according to claim 1, wherein said compound is a (+) enantiomer having an enantiomeric excess of 95%.

31. A compound according to claim 1, wherein said compound is a (+) enantiomer having an enantiomeric excess of 90%.

32. A compound according to claim 1, wherein said compound is a (−) enantiomer having an enantiomeric excess of 99%.

33. A compound according to claim 1, wherein said compound is a (−) enantiomer having an enantiomeric excess of 95%.

34. A compound according to claim 1, wherein said compound is a (−) enantiomer having an enantiomeric excess of 90%.

35. A compound according to claim 1, wherein said compound is in the form of the (R,R)-diastereomer.

36. A compound according to claim 1, wherein said compound is in the form of the (S,R)-diastereomer.

37. A compound according to claim 1, wherein said compound is in the form of the (R,S)-diastereomer.

38. A compound according to claim 1, wherein said compound is in the form of the (S,S)-diastereomer.

39. A pharmaceutical composition comprising a therapeutically effective amount of at least one compound according to claim 1 and at least one pharmaceutically acceptable carrier or excipient.

* * * * *

UNITED STATES PATENT AND TRADEMARK OFFICE
CERTIFICATE OF CORRECTION

PATENT NO. : 7,351,713 B2  Page 1 of 1
APPLICATION NO. : 10/937878
DATED : April 1, 2008
INVENTOR(S) : Laval Chan Chun Kong It is certified that error appears in the above-identified patent and that said Letters Patent is hereby corrected as shown below:

Column 90, line 1, reads "$C_{10}$ alkyl," should read -- $C_{1\text{-}10}$ alkyl, --

Signed and Sealed this

Thirtieth Day of December, 2008

JON W. DUDAS
*Director of the United States Patent and Trademark Office*